United States Patent
Morishita et al.

(10) Patent No.: US 8,455,632 B2
(45) Date of Patent: Jun. 4, 2013

(54) PRIMER SET AND PROBE FOR DETECTION OF HUMAN PAPILLOMAVIRUS

(75) Inventors: Atsushi Morishita, Osaka (JP); Isao Miyagawa, Osaka (JP); Kazuhiko Kogoh, Osaka (JP); Akiko Kawakami, Hokkaido (JP); Naoki Ogawa, Hokkaido (JP)

(73) Assignee: Kurashiki Boseki Kabushiki Kaisha, Kurashiki-shi (JP)

( * ) Notice: Subject to any disclaimer, the term of this patent is extended or adjusted under 35 U.S.C. 154(b) by 501 days.

(21) Appl. No.: 12/671,851

(22) PCT Filed: Aug. 1, 2008

(86) PCT No.: PCT/JP2008/063906
§ 371 (c)(1),
(2), (4) Date: Jun. 2, 2010

(87) PCT Pub. No.: WO2009/020079
PCT Pub. Date: Feb. 12, 2009

(65) Prior Publication Data
US 2010/0240553 A1    Sep. 23, 2010

(30) Foreign Application Priority Data
Aug. 3, 2007    (JP) .................................. 2007-203677

(51) Int. Cl.
C07H 21/04    (2006.01)
C12Q 1/68    (2006.01)
C12P 19/34    (2006.01)

(52) U.S. Cl.
USPC .................. 536/24.3; 435/6.12; 435/91.2

(58) Field of Classification Search
None
See application file for complete search history.

(56) References Cited

U.S. PATENT DOCUMENTS
6,001,612 A    12/1999    Yang
7,910,719 B2 *    3/2011    Hashimoto et al. .......... 536/24.3

2004/0265794 A1    12/2004    Yoon et al.
2005/0250092 A1    11/2005    Jeney et al.
2006/0160069 A1 *    7/2006    Chau et al. ........................ 435/5

FOREIGN PATENT DOCUMENTS
| JP | 2004-121240 A | 4/2004 |
| JP | 2005-503177 A | 2/2005 |
| JP | 2005-519611 A | 7/2005 |
| JP | 2006-345800 A | 12/2006 |
| WO | WO 03/076667 A1 | 9/2003 |
| WO | WO 2006/077102 A2 | 7/2006 |

OTHER PUBLICATIONS

Lowe et al. A computer program for selection of oligonucleotide primers for polymerase chain reaction. Nucleic Acids Res. (1990) vol. 18, No. 7, 1757-1761.*
Baay et al., Journal of Clinical Microbiology, 34(3): 745-747 (Mar. 1996).
Claas et al., American Journal of Pathology, 135(4): 703-709 (Oct. 1989).
Database EMBL [Online], EBI Accession No. EMBL: M83777 (Jun. 5, 1992).
Database EMBL [Online], EBI Accession No. EMBL: EC578383 (Jun. 23, 2006).
Database Genbank [Online], NCBI Accession No. NM_002046 (Jul. 30, 2007).
Hesselink et al., Journal of Clinical Microbiology, 43(9): 4868-4871 (Sep. 2005).
Walboomers et al., Journal of Pathology, 189: 12-19 (Sep. 1999).
Jeney et al., Journal of Virological Methods, 140: 32-42 (2007).
Sotlar et al., Journal of Clinical Microbiology, 42(7): 3176-3184 (Jul. 2004).
Database Genbank [Online], "Human papillomavirus type 66, complete genome," NCBI Accession No. U31794.1 (Oct. 18, 1995).
Reuter et al., Journal of Virology, 65(10): 5564-5568 (Oct. 1991).

* cited by examiner

Primary Examiner — Kenneth R. Horlick
Assistant Examiner — David Thomas
(74) Attorney, Agent, or Firm — Leydig, Voit & Mayer, Ltd.

(57) ABSTRACT

The invention is directed to the detection of multiple types of HPV with high specificity and high sensitivity. The invention provides primer sets, probes, and a kit containing the primer set and the probe, for type-specific HPV detection.

16 Claims, 5 Drawing Sheets

| No. | Type | Size | | No. | Type | Size |
|---|---|---|---|---|---|---|
| 1 | HPV6 | 423 | | 13 | HPV45 | 177 |
| 2 | HPV11 | 200 | | 14 | HPV51 | 381 |
| 3 | HPV16 | 238 | | 15 | HPV52 | 492 |
| 4 | HPV18 | 467 | | 16 | HPV53 | 229 |
| 5 | HPV30 | 314 | | 17 | HPV54 | 349 |
| 6 | HPV31 | 276 | | 18 | HPV56 | 236 |
| 7 | HPV33 | 476 | | 19 | HPV58 | 130 |
| 8 | HPV34 | 159 | | 20 | HPV59 | 364 |
| 9 | HPV35 | 258 | | 21 | HPV61 | 185 |
| 10 | HPV39 | 432 | | 22 | HPV66 | 233 |
| 11 | HPV40 | 417 | | 23 | HPV68 | 383 |
| 12 | HPV42 | 228 | | 24 | G3PDH | 460 |

M: φX174/Hinc II

PRIMER SET AND PROBE FOR DETECTION OF HUMAN PAPILLOMAVIRUS

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,012 bytes ASCII (Text) file named "706062SequenceListing.txt," created Feb. 1, 2010.

TECHNICAL FIELD

The present invention relates to primer set and probe for specific detection of human papillomavirus. The present invention also relates to a method for specific detection of human papillomavirus using the same.

BACKGROUND ART

Human papillomavirus (HPV) is a small size virus with cyclic double stranded DNA of about 8000 base pairs in a genome, and causes human specific infection. More than 100 kinds of HPV subtypes have been reported up to present, which are largely divided into those detected in skin lesions such as wart and the like (skin tropic HPV), and those detected in mucous membrane lesions (mucosa tropic HPV). Moreover, mucosa tropic HPV is divided into a high-risk type (HPV16, HPV18 etc.) involved in cancers such as cervical cancer, perianal cancer, penile cancer and the like, and a low-risk type (HPV6, HPV11 etc.) involved in benign condyloma acuminatum and the like. WHO estimates that HPV infection is involved in 11% of malignant tumors of women around the world or about 450,000 people, and there are 300 million HPV infection carriers in the world, suggesting that HPV is an ordinary virus. Particularly, HPV is almost always detected in cervical cancer patients.

Cervical cancer is the second highest in number among the cancers of women in the world, and about 250,000 people in the world, and about 2500 people in Japan die of cervical cancer annually. Thus, the prophylaxis, diagnosis, and treatment of cervical cancer have been recognized as highly important issues for the women's health. Fortunately, prophylaxis of cervical cancer is possible. The reasons therefor are that dysplasia, which is a precancerous lesion of cervical cancer, can be found by cytological diagnosis and the like, and dysplasia can be cured by a simple treatment. Since dysplasia is caused by HPV infection, the importance of HPV genetic screening, which enables earlier and more certain discovery of cervical cancer or precancerous lesion, has been increasingly recognized.

The method of HPV genetic screening is largely divided into a method including direct detection of HPV DNA, and a method including amplification of HPV DNA by polymerase chain reaction (PCR) before detection of the DNA.

A representative method without using PCR is a hybrid capture method. In this method, RNA probe is hybridized with HPV DNA in a sample, and the resulting DNA/RNA hybrid is detected by immunoassay using an antibody. Being convenient, this method is currently a main method for HPV genetic screening. On the other hand, the method has low reliability due to low sensitivity, low stability caused by the use of RNA probe, and uneliminatable possibility of contamination. Moreover, even though this method can be used to identify whether the infected HPV is of a high-risk type or a low-risk type, it cannot identify its subtype.

In a method utilizing PCR, amplified DNA is detected by a method including cleavage with a restriction enzyme and electrophoresis to detect bands, or a method including hybridization with a probe on DNA microarray for detection. The former detection method utilizing electrophoresis can be performed in a general laboratory facility and is superior in the economic aspect. As defects, however, it requires complicated processes and incompletely identifies subtypes. On the other hand, the latter detection method utilizing hybridization with a probe shows high detection sensitivity and high specificity of subtype identification. However, it has problems in the rapidness and the economic aspect.

As for DNA amplification by PCR, a method of type-specific amplification of HPV gene using a type-specific primer, and a method of non-type-specific amplification of HPV gene using a random primer or non-type-specific primer are known.

In the methods disclosed in patent documents 1 and 2, DNA is amplified by PCR using a type-specific primer. The amplified DNA is subjected to hybridization with DNA microarray in patent document 1 using an amplified double stranded DNA per se as a probe, and subjected to electrophoresis in patent document 2 to detect presence or absence of HPV DNA. These methods achieve amplification with high specificity and high sensitivity by the use of a type-specific primer. Even when a mixture of primers is used, they can specifically detect a particular type of HPV.

On the other hand, in the method disclosed in patent document 3, HPV DNA is amplified using a non-type-specific primer, and hybridized with DNA microarray using a short single strand oligo DNA as a probe to detect HPV DNA. Since this method uses a common primer, it is advantageous in the synthesis cost and easiness of design. However, overall sensitivity is low even if low specificity and low sensitivity in PCR are overcome to a certain degree by increasing the specificity of hybridization by the use of a short probe. Even though a primer is prepared for each HPV type in the method disclosed in patent document 4, since the respective primer sequences are almost the same, the method of preparing the primers is considered to be almost the same as in patent document 3.

As the situation stands, a method capable of detecting multiple types of HPV with high specificity and high sensitivity, which is superior in rapidness, convenience and economic aspects needs to be developed.

[patent document 1] JP-A-2004-121240
[patent document 2] JP-A-2006-345800
[patent document 3] Patent Application Publication No. 2005-503177
[patent document 4] Patent Application Publication No. 2005-519611

DISCLOSURE OF THE INVENTION

Problems to be Solved by the Invention

The present invention aims to provide primer set and probe for detection of multiple types of HPV with high specificity and high sensitivity. The present invention also aims to provide a method for the detection of multiple types of HPV with high specificity and high sensitivity utilizing the aforementioned primer set and probe.

Means of Solving the Problems

In an attempt to solve the aforementioned problems, the present inventors have taken note of a detection method of HPV gene, comprising amplifying HPV gene by PCR using a type-specific primer and hybridizing a PCR amplification product with DNA microarray for the detection, and conducted intensive studies. As a result, they have found that multiple types of HPV can be detected rapidly and conveniently with high specificity and high sensitivity by the use of the primer sets and probes of the present invention, which resulted in the completion of the present invention.

Accordingly, the present invention provides the following.

[1] A PCR primer set for amplification of human papillomavirus (HPV) gene, which is at least one kind selected from the group consisting of (1) primer set 1 consisting of a primer comprising the base sequence shown by SEQ ID NO: 1 or a variant thereof similarly having a function as a primer and comprising a base sequence that hybridizes with the base sequence complementary to the base sequence shown by SEQ ID NO: 1 under stringent conditions, and a primer comprising the base sequence shown by SEQ ID NO: 2 or a variant thereof similarly having a function as a primer and comprising a base sequence that hybridizes with the base sequence complementary to the base sequence shown by SEQ ID NO: 2 under stringent conditions, (2) primer set 2 consisting of a primer comprising the base sequence shown by SEQ ID NO: 3 or a variant thereof similarly having a function as a primer and comprising a base sequence that hybridizes with the base sequence complementary to the base sequence shown by SEQ ID NO: 3 under stringent conditions, and a primer comprising the base sequence shown by SEQ ID NO: 4 or a variant thereof similarly having a function as a primer and comprising a base sequence that hybridizes with the base sequence complementary to the base sequence shown by SEQ ID NO: 4 under stringent conditions, (3) primer set 3 consisting of a primer comprising the base sequence shown by SEQ ID NO: 5 or a variant thereof similarly having a function as a primer and comprising a base sequence that hybridizes with the base sequence complementary to the base sequence shown by SEQ ID NO: 5 under stringent conditions, and a primer comprising the base sequence shown by SEQ ID NO: 6 or a variant thereof similarly having a function as a primer and comprising a base sequence that hybridizes with the base sequence complementary to the base sequence shown by SEQ ID NO: 6 under stringent conditions, (4) primer set 4 consisting of a primer comprising the base sequence shown by SEQ ID NO: 7 or a variant thereof similarly having a function as a primer and comprising a base sequence that hybridizes with the base sequence complementary to the base sequence shown by SEQ ID NO: 7 under stringent conditions, and a primer comprising the base sequence shown by SEQ ID NO: 8 or a variant thereof similarly having a function as a primer and comprising a base sequence that hybridizes with the base sequence complementary to the base sequence shown by SEQ ID NO: 8 under stringent conditions, (5) primer set 5 consisting of a primer comprising the base sequence shown by SEQ ID NO: 9 or a variant thereof similarly having a function as a primer and comprising a base sequence that hybridizes with the base sequence complementary to the base sequence shown by SEQ ID NO: 9 under stringent conditions, and a primer comprising the base sequence shown by SEQ ID NO: 10 or a variant thereof similarly having a function as a primer and comprising a base sequence that hybridizes with the base sequence complementary to the base sequence shown by SEQ ID NO: 10 under stringent conditions, (6) primer set 6 consisting of a primer comprising the base sequence shown by SEQ ID NO: 11 or a variant thereof similarly having a function as a primer and comprising a base sequence that hybridizes with the base sequence complementary to the base sequence shown by SEQ ID NO: 11 under stringent conditions, and a primer comprising the base sequence shown by SEQ ID NO: 12 or a variant thereof similarly having a function as a primer and comprising a base sequence that hybridizes with the base sequence complementary to the base sequence shown by SEQ ID NO: 12 under stringent conditions, (7) primer set 7 consisting of a primer comprising the base sequence shown by SEQ ID NO: 13 or a variant thereof similarly having a function as a primer and comprising a base sequence that hybridizes with the base sequence complementary to the base sequence shown by SEQ ID NO: 13 under stringent conditions, and a primer comprising the base sequence shown by SEQ ID NO: 14 or a variant thereof similarly having a function as a primer and comprising a base sequence that hybridizes with the base sequence complementary to the base sequence shown by SEQ ID NO: 14 under stringent conditions, (8) primer set 8 consisting of a primer comprising the base sequence shown by SEQ ID NO: 15 or a variant thereof similarly having a function as a primer and comprising a base sequence that hybridizes with the base sequence complementary to the base sequence shown by SEQ ID NO: 15 under stringent conditions, and a primer comprising the base sequence shown by SEQ ID NO: 16 or a variant thereof similarly having a function as a primer and comprising a base sequence that hybridizes with the base sequence complementary to the base sequence shown by SEQ ID NO: 16 under stringent conditions, (9) primer set 9 consisting of a primer comprising the base sequence shown by SEQ ID NO: 17 or a variant thereof similarly having a function as a primer and comprising a base sequence that hybridizes with the base sequence complementary to the base sequence shown by SEQ ID NO: 17 under stringent conditions, and a primer comprising the base sequence shown by SEQ ID NO: 18 or a variant thereof similarly having a function as a primer and comprising a base sequence that hybridizes with the base sequence complementary to the base sequence shown by SEQ ID NO: 18 under stringent conditions,

(10) primer set 10 consisting of a primer comprising the base sequence shown by SEQ ID NO: 19 or a variant thereof similarly having a function as a primer and comprising a base sequence that hybridizes with the base sequence complementary to the base sequence shown by SEQ ID NO: 19 under stringent conditions, and a primer comprising the base sequence shown by SEQ ID NO: 20 or a variant thereof similarly having a function as a primer and comprising a base sequence that hybridizes with the base sequence complementary to the base sequence shown by SEQ ID NO: 20 under stringent conditions,

(11) primer set 11 consisting of a primer comprising the base sequence shown by SEQ ID NO: 21 or a variant thereof similarly having a function as a primer and comprising a base sequence that hybridizes with the base sequence complementary to the base sequence shown by SEQ ID NO: 21 under stringent conditions, and a primer comprising the base sequence shown by SEQ ID NO: 22 or a variant thereof similarly having a function as a primer and comprising a base sequence that hybridizes with the base sequence complementary to the base sequence shown by SEQ ID NO: 22 under stringent conditions,

(12) primer set 12 consisting of a primer comprising the base sequence shown by SEQ ID NO: 23 or a variant thereof similarly having a function as a primer and comprising a base sequence that hybridizes with the base sequence complementary to the base sequence shown by SEQ ID NO: 23 under stringent conditions, and a primer comprising the base sequence shown by SEQ ID NO: 24 or a variant thereof similarly having a function as a primer and comprising a base sequence that hybridizes with the base sequence complementary to the base sequence shown by SEQ ID NO: 24 under stringent conditions,

(13) primer set 13 consisting of a primer comprising the base sequence shown by SEQ ID NO: 25 or a variant thereof similarly having a function as a primer and comprising a base sequence that hybridizes with the base sequence complementary to the base sequence shown by SEQ ID NO: 25 under stringent conditions, and a primer comprising the base sequence shown by SEQ ID NO: 26 or a variant thereof similarly having a function as a primer and comprising a base sequence that hybridizes with the base sequence complementary to the base sequence shown by SEQ ID NO: 26 under stringent conditions,

(14) primer set 14 consisting of a primer comprising the base sequence shown by SEQ ID NO: 27 or a variant thereof similarly having a function as a primer and comprising a base sequence that hybridizes with the base sequence complementary to the base sequence shown by SEQ ID NO: 27 under stringent conditions, and a primer comprising the base sequence shown by SEQ ID NO: 28 or a variant thereof similarly having a function as a primer and comprising a base sequence that hybridizes with the base sequence complementary to the base sequence shown by SEQ ID NO: 28 under stringent conditions,

(15) primer set 15 consisting of a primer comprising the base sequence shown by SEQ ID NO: 29 or a variant thereof similarly having a function as a primer and comprising a base sequence that hybridizes with the base sequence complementary to the base sequence shown by SEQ ID NO: 29 under stringent conditions, and a primer comprising the base sequence shown by SEQ ID NO: 30 or a variant thereof similarly having a function as a primer and comprising a base sequence that hybridizes with the base sequence complementary to the base sequence shown by SEQ ID NO: 30 under stringent conditions,

(16) primer set 16 consisting of a primer comprising the base sequence shown by SEQ ID NO: 31 or a variant thereof similarly having a function as a primer and comprising a base sequence that hybridizes with the base sequence complementary to the base sequence shown by SEQ ID NO: 31 under stringent conditions, and a primer comprising the base sequence shown by SEQ ID NO: 32 or a variant thereof similarly having a function as a primer and comprising a base sequence that hybridizes with the base sequence complementary to the base sequence shown by SEQ ID NO: 32 under stringent conditions,

(17) primer set 17 consisting of a primer comprising the base sequence shown by SEQ ID NO: 33 or a variant thereof similarly having a function as a primer and comprising a base sequence that hybridizes with the base sequence complementary to the base sequence shown by SEQ ID NO: 33 under stringent conditions, and a primer comprising the base sequence shown by SEQ ID NO: 34 or a variant thereof similarly having a function as a primer and comprising a base sequence that hybridizes with the base sequence complementary to the base sequence shown by SEQ ID NO: 34 under stringent conditions,

(18) primer set 18 consisting of a primer comprising the base sequence shown by SEQ ID NO: 35 or a variant thereof similarly having a function as a primer and comprising a base sequence that hybridizes with the base sequence complementary to the base sequence shown by SEQ ID NO: 35 under stringent conditions, and a primer comprising the base sequence shown by SEQ ID NO: 36 or a variant thereof similarly having a function as a primer and comprising a base sequence that hybridizes with the base sequence complementary to the base sequence shown by SEQ ID NO: 36 under stringent conditions,

(19) primer set 19 consisting of a primer comprising the base sequence shown by SEQ ID NO: 37 or a variant thereof similarly having a function as a primer and comprising a base sequence that hybridizes with the base sequence complementary to the base sequence shown by SEQ ID NO: 37 under stringent conditions, and a primer comprising the base sequence shown by SEQ ID NO: 38 or a variant thereof similarly having a function as a primer and comprising a base sequence that hybridizes with the base sequence complementary to the base sequence shown by SEQ ID NO: 38 under stringent conditions,

(20) primer set 20 consisting of a primer comprising the base sequence shown by SEQ ID NO: 39 or a variant thereof similarly having a function as a primer and comprising a base sequence that hybridizes with the base sequence complementary to the base sequence shown by SEQ ID NO: 39 under stringent conditions, and a primer comprising the base sequence shown by SEQ ID NO: 40 or a variant thereof similarly having a function as a primer and comprising a base sequence that hybridizes with the base sequence complementary to the base sequence shown by SEQ ID NO: 40 under stringent conditions,

(21) primer set 21 consisting of a primer comprising the base sequence shown by SEQ ID NO: 41 or a variant thereof similarly having a function as a primer and comprising a base sequence that hybridizes with the base sequence complementary to the base sequence shown by SEQ ID NO: 41 under stringent conditions, and a primer comprising the base sequence shown by SEQ ID NO: 42 or a variant thereof similarly having a function as a primer and comprising a base sequence that hybridizes with the base sequence complementary to the base sequence shown by SEQ ID NO: 42 under stringent conditions,

(22) primer set 22 consisting of a primer comprising the base sequence shown by SEQ ID NO: 43 or a variant thereof similarly having a function as a primer and comprising a base sequence that hybridizes with the base sequence complementary to the base sequence shown by SEQ ID NO: 43 under stringent conditions, and a primer comprising the base sequence shown by SEQ ID NO: 44 or a variant thereof similarly having a function as a primer and comprising a base sequence that hybridizes with the base sequence complementary to the base sequence shown by SEQ ID NO: 44 under stringent conditions, and

(23) primer set 23 consisting of a primer comprising the base sequence shown by SEQ ID NO: 45 or a variant thereof similarly having a function as a primer and comprising a base sequence that hybridizes with the base sequence complementary to the base sequence shown by SEQ ID NO: 45 under stringent conditions, and a primer comprising the base sequence shown by SEQ ID NO: 46 or a variant thereof similarly having a function as a primer and comprising a base sequence that hybridizes with the base sequence complementary to the base sequence shown by SEQ ID NO: 46 under stringent conditions.

[2] A probe for detection of human papillomavirus (HPV), which is at least one kind selected from the group consisting of (1) a probe comprising the base sequence shown by SEQ ID NO: 49 or a variant thereof similarly having a function as a probe and comprising a base sequence that hybridizes with the base sequence complementary to the base sequence shown by SEQ ID NO: 49 under stringent conditions, or a probe comprising the base sequence complementary to the base sequence shown by SEQ ID NO: 49 or a variant thereof similarly having a function as a probe and comprising a base sequence that hybridizes with the base sequence shown by SEQ ID NO: 49 under stringent conditions (probe 1), (2) a probe comprising the base sequence shown by SEQ ID NO: 50 or a variant thereof similarly having a function as a probe and comprising a base sequence that hybridizes with the base sequence complementary to the base sequence shown by SEQ ID NO: 50 under stringent conditions, or a probe comprising the base sequence complementary to the base sequence shown by SEQ ID NO: 50 or a variant thereof similarly having a function as a probe and comprising a base sequence that hybridizes with the base sequence shown by SEQ ID NO: 50 under stringent conditions (probe 2), (3) a probe comprising the base sequence shown by SEQ ID NO: 51 or a variant thereof similarly having a function as a probe and comprising a base sequence that hybridizes with the base sequence complementary to the base sequence shown by SEQ ID NO: 51 under stringent conditions, or a probe comprising the base sequence complementary to the base sequence shown by SEQ ID NO: 51 or a variant thereof similarly having a function as a probe and comprising a base sequence that hybridizes with the base sequence shown by SEQ ID NO: 51 under stringent conditions (probe 3), (4) a probe comprising the base sequence shown by SEQ ID NO: 52 or a variant thereof similarly having a function as a probe and comprising a base sequence that hybridizes with the base sequence complementary to the base sequence shown by SEQ ID NO: 52 under stringent conditions, or a probe comprising the base sequence complementary to the base sequence shown by SEQ ID NO: 52 or a variant thereof similarly having a function as a probe and comprising a base sequence that hybridizes with the base sequence shown by SEQ ID NO: 52 under stringent conditions (probe 4), (5) a probe comprising the base sequence shown by SEQ ID NO: 53 or a variant thereof similarly having a function as a probe and comprising a base sequence that hybridizes with the base sequence complementary to the base sequence shown by SEQ ID NO: 53 under stringent conditions, or a probe comprising the base sequence complementary to the base sequence shown by SEQ ID NO: 53 or a variant thereof similarly having a function as a probe and comprising a base sequence that hybridizes with the base sequence shown by SEQ ID NO: 53 under stringent conditions (probe 5), (6) a probe comprising the base sequence shown by SEQ ID NO: 54 or a variant thereof similarly having a function as a probe and comprising a base sequence that hybridizes with the base sequence complementary to the base sequence shown by SEQ ID NO: 54 under stringent conditions, or a probe comprising the base sequence complementary to the base sequence shown by SEQ ID NO: 54 or a variant thereof similarly having a function as a probe and comprising a base sequence that hybridizes with the base sequence shown by SEQ ID NO: 54 under stringent conditions (probe 6), (7) a probe comprising the base sequence shown by SEQ ID NO: 55 or a variant thereof similarly having a function as a probe and comprising a base sequence that hybridizes with the base sequence complementary to the base sequence shown by SEQ ID NO: 55 under stringent conditions, or a probe comprising the base sequence complementary to the base sequence shown by SEQ ID NO: 55 or a variant thereof similarly having a function as a probe and comprising a base sequence that hybridizes with the base sequence shown by SEQ ID NO: 55 under stringent conditions (probe 7), (8) a probe comprising the base sequence shown by SEQ ID NO: 56 or a variant thereof similarly having a function as a probe and comprising a base sequence that hybridizes with the base sequence complementary to the base sequence shown by SEQ ID NO: 56 under stringent conditions, or a probe comprising the base sequence complementary to the base sequence shown by SEQ ID NO: 56 or a variant thereof similarly having a function as a probe and comprising a base sequence that hybridizes with the base sequence shown by SEQ ID NO: 56 under stringent conditions (probe 8), (9) a probe comprising the base sequence shown by SEQ ID NO: 57 or a variant thereof similarly having a function as a probe and comprising a base sequence that hybridizes with the base sequence complementary to the base sequence shown by SEQ ID NO: 57 under stringent conditions, or a probe comprising the base sequence complementary to the base sequence shown by SEQ ID NO: 57 or a variant thereof similarly having a function as a probe and comprising a base sequence that hybridizes with the base sequence shown by SEQ ID NO: 57 under stringent conditions (probe 9),

(10) a probe comprising the base sequence shown by SEQ ID NO: 58 or a variant thereof similarly having a function as a probe and comprising a base sequence that hybridizes with the base sequence complementary to the base sequence shown by SEQ ID NO: 58 under stringent conditions, or a probe comprising the base sequence complementary to the base sequence shown by SEQ ID NO: 58 or a variant thereof similarly having a function as a probe and comprising a base sequence that hybridizes with the base sequence shown by SEQ ID NO: 58 under stringent conditions (probe 10),

(11) a probe comprising the base sequence shown by SEQ ID NO: 59 or a variant thereof similarly having a function as a probe and comprising a base sequence that hybridizes with the base sequence complementary to the base sequence shown by SEQ ID NO: 59 under stringent conditions, or a probe comprising the base sequence complementary to the base sequence shown by SEQ ID NO: 59 or a variant thereof similarly having a function as a probe and comprising a base sequence that hybridizes with the base sequence shown by SEQ ID NO: 59 under stringent conditions (probe 11),

(12) a probe comprising the base sequence shown by SEQ ID NO: 60 or a variant thereof similarly having a function as a probe and comprising a base sequence that hybridizes with the base sequence complementary to the base sequence shown by SEQ ID NO: 60 under stringent conditions, or a probe comprising the base sequence complementary to the base sequence shown by SEQ ID NO: 60 or a variant thereof similarly having a function as a probe and comprising a base sequence that hybridizes with the base sequence shown by SEQ ID NO: 60 under stringent conditions (probe 12),

(13) a probe comprising the base sequence shown by SEQ ID NO: 61 or a variant thereof similarly having a function as a probe and comprising a base sequence that hybridizes with the base sequence complementary to the base sequence shown by SEQ ID NO: 61 under stringent conditions, or a probe comprising the base sequence complementary to the base sequence shown by SEQ ID NO: 61 or a variant thereof similarly having a function as a probe and comprising a base sequence that hybridizes with the base sequence shown by SEQ ID NO: 61 under stringent conditions (probe 13),

(14) a probe comprising the base sequence shown by SEQ ID NO: 62 or a variant thereof similarly having a function as a probe and comprising a base sequence that hybridizes with the base sequence complementary to the base sequence shown by SEQ ID NO: 62 under stringent conditions, or a probe comprising the base sequence complementary to the base sequence shown by SEQ ID NO: 62 or a variant thereof similarly having a function as a probe and comprising a base sequence that hybridizes with the base sequence shown by SEQ ID NO: 62 under stringent conditions (probe 14),

(15) a probe comprising the base sequence shown by SEQ ID NO: 63 or a variant thereof similarly having a function as a probe and comprising a base sequence that hybridizes with the base sequence complementary to the base sequence shown by SEQ ID NO: 63 under stringent conditions, or a probe comprising the base sequence complementary to the base sequence shown by SEQ ID NO: 63 or a variant thereof similarly having a function as a probe and comprising a base sequence that hybridizes with the base sequence shown by SEQ ID NO: 63 under stringent conditions (probe 15),

(16) a probe comprising the base sequence shown by SEQ ID NO: 64 or a variant thereof similarly having a function as a probe and comprising a base sequence that hybridizes with the base sequence complementary to the base sequence shown by SEQ ID NO: 64 under stringent conditions, or a probe comprising the base sequence complementary to the base sequence shown by SEQ ID NO: 64 or a variant thereof similarly having a function as a probe and comprising a base sequence that hybridizes with the base sequence shown by SEQ ID NO: 64 under stringent conditions (probe 16),

(17) a probe comprising the base sequence shown by SEQ ID NO: 65 or a variant thereof similarly having a function as a probe and comprising a base sequence that hybridizes with the base sequence complementary to the base sequence shown by SEQ ID NO: 65 under stringent conditions, or a probe comprising the base sequence complementary to the base sequence shown by SEQ ID NO: 65 or a variant thereof similarly having a function as a probe and comprising a base sequence that hybridizes with the base sequence shown by SEQ ID NO: 65 under stringent conditions (probe 17),

(18) a probe comprising the base sequence shown by SEQ ID NO: 66 or a variant thereof similarly having a function as a probe and comprising a base sequence that hybridizes with the base sequence complementary to the base sequence shown by SEQ ID NO: 66 under stringent conditions, or a probe comprising the base sequence complementary to the base sequence shown by SEQ ID NO: 66 or a variant thereof similarly having a function as a probe and comprising a base sequence that hybridizes with the base sequence shown by SEQ ID NO: 66 under stringent conditions (probe 18),

(19) a probe comprising the base sequence shown by SEQ ID NO: 67 or a variant thereof similarly having a function as a probe and comprising a base sequence that hybridizes with the base sequence complementary to the base sequence shown by SEQ ID NO: 67 under stringent conditions, or a probe comprising the base sequence complementary to the base sequence shown by SEQ ID NO: 67 or a variant thereof similarly having a function as a probe and comprising a base sequence that hybridizes with the base sequence shown by SEQ ID NO: 67 under stringent conditions (probe 19),

(20) a probe comprising the base sequence shown by SEQ ID NO: 68 or a variant thereof similarly having a function as a probe and comprising a base sequence that hybridizes with the base sequence complementary to the base sequence shown by SEQ ID NO: 68 under stringent conditions, or a probe comprising the base sequence complementary to the base sequence shown by SEQ ID NO: 68 or a variant thereof similarly having a function as a probe and comprising a base sequence that hybridizes with the base sequence shown by SEQ ID NO: 68 under stringent conditions (probe 20),

(21) a probe comprising the base sequence shown by SEQ ID NO: 69 or a variant thereof similarly having a function as a probe and comprising a base sequence that hybridizes with the base sequence complementary to the base sequence shown by SEQ ID NO: 69 under stringent conditions, or a probe comprising the base sequence complementary to the base sequence shown by SEQ ID NO: 69 or a variant thereof similarly having a function as a probe and comprising a base sequence that hybridizes with the base sequence shown by SEQ ID NO: 69 under stringent conditions (probe 21),

(22) a probe comprising the base sequence shown by SEQ ID NO: 70 or a variant thereof similarly having a function as a probe and comprising a base sequence that hybridizes with the base sequence complementary to the base sequence shown by SEQ ID NO: 70 under stringent conditions, or a probe comprising the base sequence complementary to the base sequence shown by SEQ ID NO: 70 or a variant thereof similarly having a function as a probe and comprising a base sequence that hybridizes with the base sequence shown by SEQ ID NO: 70 under stringent conditions (probe 22), and

(23) a probe comprising the base sequence shown by SEQ ID NO: 71 or a variant thereof similarly having a function as a probe and comprising a base sequence that hybridizes with the base sequence complementary to the base sequence shown by SEQ ID NO: 71 under stringent conditions, or a probe comprising the base sequence complementary to the base sequence shown by SEQ ID NO: 71 or a variant thereof similarly having a function as a probe and comprising a base sequence that hybridizes with the base sequence shown by SEQ ID NO: 71 under stringent conditions (probe 23).

[3] A kit for detection of human papillomavirus (HPV), comprising (1) a combination of primer set 1 and probe 1, (2) a combination of primer set 2 and probe 2, (3) a combination of primer set 3 and probe 3, (4) a combination of primer set 4 and probe 4, (5) a combination of primer set 5 and probe 5, (6) a combination of primer set 6 and probe 6, (7) a combination of primer set 7 and probe 7, (8) a combination of primer set 8 and probe 8, (9) a combination of primer set 9 and probe 9, (10) a combination of primer set 10 and probe 10, (11) a combination of primer set 11 and probe 11, (12) a combination of primer set 12 and probe 12, (13) a combination of primer set 13 and probe 13, (14) a combination of primer set 14 and probe 14, (15) a combination of primer set 15 and probe 15, (16) a combination of primer set 16 and probe 16, (17) a combination of primer set 17 and probe 17, (18) a combination of primer set 18 and probe 18, (19) a combination of primer set 19 and probe 19, (20) a combination of primer set 20 and probe 20, (21) a combination of primer set 21 and probe 21, (22) a combination of primer set 22 and probe 22, and (23) a combination of primer set 23 and probe 23, and optionally (24) a combination of primer set 24 and probe 24.

[4] The kit of the above-mentioned [3], comprising two or more combinations selected from the group consisting of the above-mentioned combinations (1) to (23).

[5] The kit of the above-mentioned [3] or [4], comprising a combination of primer set 3 and probe 3, and a combination of primer set 4 and probe 4, and optionally a combination of primer set 24 and probe 24.

[6] The kit of the above-mentioned [3] or [4], comprising a combination of primer set 3 and probe 3, a combination of primer set 4 and probe 4, a combination of primer set 5 and probe 5, a combination of primer set 6 and probe 6, a combination of primer set 7 and probe 7, a combination of primer set 9 and probe 9, a combination of primer set 10 and probe 10, a combination of primer set 13 and probe 13, a combination of primer set 14 and probe 14, a combination of primer set 15 and probe 15, a combination of primer set 18 and probe 18, a combination of primer set 19 and probe 19, a combination of primer set 20 and probe 20, and a combination of primer set 23 and probe 23, and optionally a combination of primer set 24 and probe 24.

[7] The kit of the above-mentioned [3] or [4], comprising a combination of primer set 1 and probe 1, a combination of primer set 2 and probe 2, a combination of primer set 3 and probe 3, a combination of primer set 4 and probe 4, a combination of primer set 5 and probe 5, a combination of primer set 6 and probe 6, a combination of primer set 7 and probe 7, a combination of primer set 8 and probe 8, a combination of primer set 9 and probe 9, a combination of primer set 10 and probe 10, a combination of primer set 11 and probe 11, a combination of primer set 12 and probe 12, a combination of primer set 13 and probe 13, a combination of primer set 14 and probe 14, a combination of primer set 15 and probe 15, a combination of primer set 16 and probe 16, a combination of primer set 17 and probe 17, a combination of primer set 18 and probe 18, a combination of primer set 19 and probe 19, a combination of primer set 20 and probe 20, a combination of primer set 21 and probe 21, a combination of primer set 22 and probe 22, and a combination of primer set 23 and probe 23, and optionally a combination of primer set 24 and probe 24.

[8] A method of type-specifically detecting the presence or absence of HPV in a sample by using the kit of any one of the above-mentioned [3] to [7], comprising a step of performing PCR using the aforementioned primer set and DNA extracted from the sample as a template, and a step of detecting an amplified DNA product.

[9] A method of type-specifically detecting the presence or absence of HPV in a sample by using the kit of any one of the above-mentioned [3] to [7], comprising a step of performing PCR using the aforementioned primer set and DNA extracted from the sample as a template, a step of processing an amplified DNA product to have a single strand, and a step of hybridizing the single strand DNA with the aforementioned probe, followed by detection.

[10] A DNA microarray for detection of HPV, wherein at least one kind of probe selected from the group consisting of probes 1 to 23 described in the above-mentioned [2] is immobilized.

[11] The DNA microarray of the above-mentioned [10], wherein two or more probes selected from the group consisting of probes 1 to 23 described in the above-mentioned [2] are immobilized.

[12] The DNA microarray of the above-mentioned [10] or [11], wherein probe 24 is immobilized.

Effect of the Invention

The present invention provides primer set and probe capable of rapidly and conveniently detecting multiple types of HPV with high specificity and high sensitivity. The present invention also provides a method capable of rapidly and conveniently detecting multiple types of HPV with high specificity and high sensitivity by utilizing the aforementioned primer sets and probes.

BEST MODE FOR CARRYING OUT THE INVENTION

Figure 1:
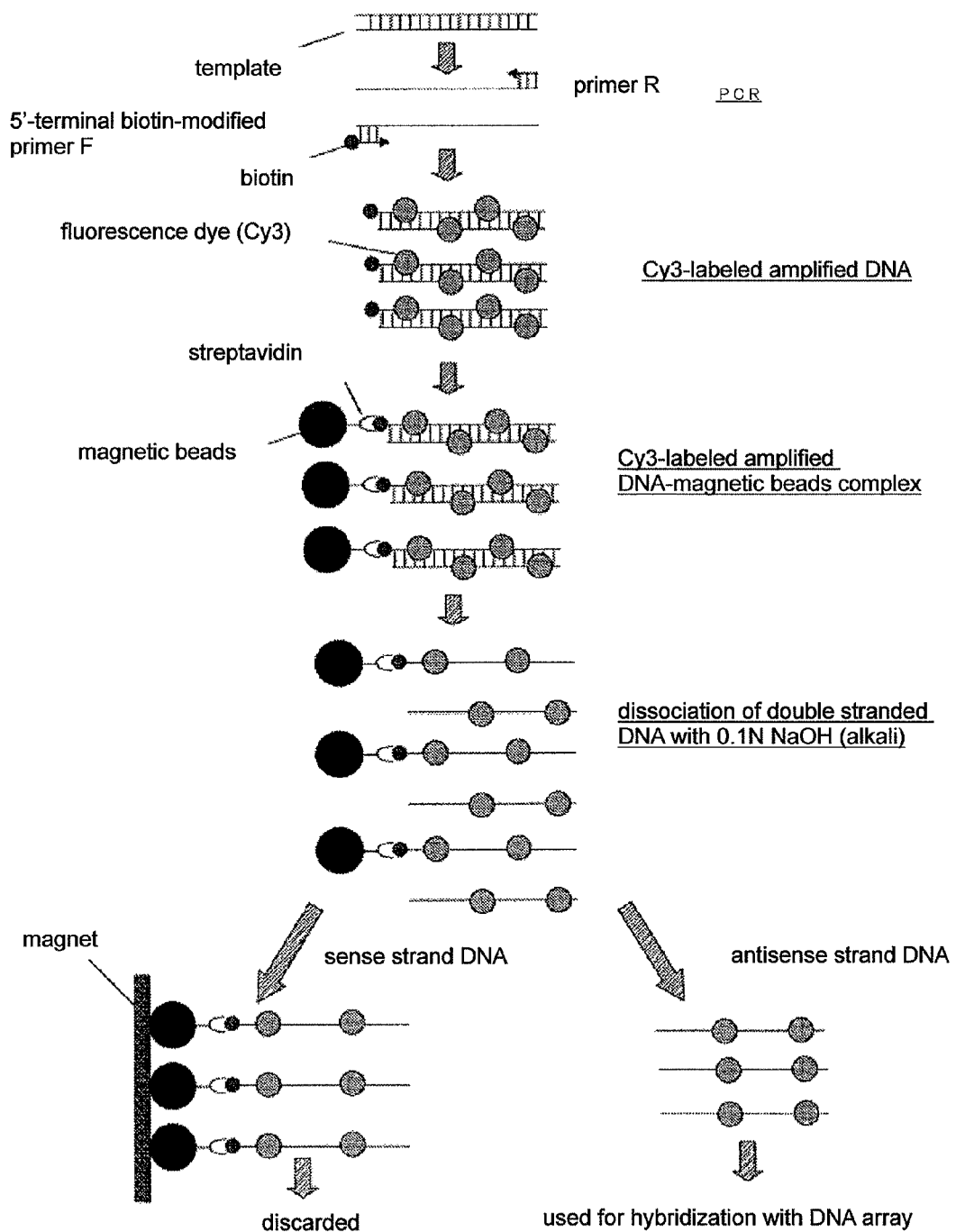
FIG. 1 shows a conceptional drawing of an isolation step (isolation of antisense strand DNA) of single strand DNA using magnetic beads.

The present invention provides PCR primer set for amplifying HPV gene, particularly type-specific primer set. Examples of the primer set include primer sets shown of the following (1) to (23).

(1) primer set 1 consisting of a primer comprising the base sequence shown by SEQ ID NO: 1 or a variant thereof similarly having a function as a primer and comprising a base sequence that hybridizes with the base sequence complementary to the base sequence shown by SEQ ID NO: 1 under stringent conditions, and a primer comprising the base sequence shown by SEQ ID NO: 2 or a variant thereof similarly having a function as a primer and comprising a base sequence that hybridizes with the base sequence complementary to the base sequence shown by SEQ ID NO: 2 under stringent conditions, (2) primer set 2 consisting of a primer comprising the base sequence shown by SEQ ID NO: 3 or a variant thereof similarly having a function as a primer and comprising a base sequence that hybridizes with the base sequence complementary to the base sequence shown by SEQ ID NO: 3 under stringent conditions, and a primer comprising the base sequence shown by SEQ ID NO: 4 or a variant thereof similarly having a function as a primer and comprising a base sequence that hybridizes with the base sequence complementary to the base sequence shown by SEQ ID NO: 4 under stringent conditions, (3) primer set 3 consisting of a primer comprising the base sequence shown by SEQ ID NO: 5 or a variant thereof similarly having a function as a primer and comprising a base sequence that hybridizes with the base sequence complementary to the base sequence shown by SEQ ID NO: 5 under stringent conditions, and a primer comprising the base sequence shown by SEQ ID NO: 6 or a variant thereof similarly having a function as a primer and comprising a base sequence that hybridizes with the base sequence complementary to the base sequence shown by SEQ ID NO: 6 under stringent conditions, (4) primer set 4 consisting of a primer comprising the base sequence shown by SEQ ID NO: 7 or a variant thereof similarly having a function as a primer and comprising a base sequence that hybridizes with the base sequence complementary to the base sequence shown by SEQ ID NO: 7 under stringent conditions, and a primer comprising the base sequence shown by SEQ ID NO: 8 or a variant thereof similarly having a function as a primer and comprising a base sequence that hybridizes with the base sequence complementary to the base sequence shown by SEQ ID NO: 8 under stringent conditions, (5) primer set 5 consisting of a primer comprising the base sequence shown by SEQ ID NO: 9 or a variant thereof similarly having a function as a primer and comprising a base sequence that hybridizes with the base sequence complementary to the base sequence shown by SEQ ID NO: 9 under stringent conditions, and a primer comprising the base sequence shown by SEQ ID NO: 10 or a variant thereof similarly having a function as a primer and comprising a base sequence that hybridizes with the base sequence complementary to the base sequence shown by SEQ ID NO: 10 under stringent conditions, (6) primer set 6 consisting of a primer comprising the base sequence shown by SEQ ID NO: 11 or a variant thereof similarly having a function as a primer and comprising a base sequence that hybridizes with the base sequence complementary to the base sequence shown by SEQ ID NO: 11 under stringent conditions, and a primer comprising the base sequence shown by SEQ ID NO: 12 or a variant thereof similarly having a function as a primer and comprising a base sequence that hybridizes with the base sequence complementary to the base sequence shown by SEQ ID NO: 12 under stringent conditions, (7) primer set 7 consisting of a primer comprising the base sequence shown by SEQ ID NO: 13 or a variant thereof similarly having a function as a primer and comprising a base sequence that hybridizes with the base sequence complementary to the base sequence shown by SEQ ID NO: 13 under stringent conditions, and a primer comprising the base sequence shown by SEQ ID NO: 14 or a variant thereof similarly having a function as a primer and comprising a base sequence that hybridizes with the base sequence complementary to the base sequence shown by SEQ ID NO: 14 under stringent conditions, (8) primer set 8 consisting of a primer comprising the base sequence shown by SEQ ID NO: 15 or a variant thereof similarly having a function as a primer and comprising a base sequence that hybridizes with the base sequence complementary to the base sequence shown by SEQ ID NO: 15 under stringent conditions, and a primer comprising the base sequence shown by SEQ ID NO: 16 or a variant thereof similarly having a function as a primer and comprising a base sequence that hybridizes with the base sequence complementary to the base sequence shown by SEQ ID NO: 16 under stringent conditions, (9) primer set 9 consisting of a primer comprising the base sequence shown by SEQ ID NO: 17 or a variant thereof similarly having a function as a primer and comprising a base sequence that hybridizes with the base sequence complementary to the base sequence shown by SEQ ID NO: 17 under stringent conditions, and a primer comprising the base sequence shown by SEQ ID NO: 18 or a variant thereof similarly having a function as a primer and comprising a base sequence that hybridizes with the base sequence complementary to the base sequence shown by SEQ ID NO: 18 under stringent conditions,

(10) primer set 10 consisting of a primer comprising the base sequence shown by SEQ ID NO: 19 or a variant thereof similarly having a function as a primer and comprising a base sequence that hybridizes with the base sequence complementary to the base sequence shown by SEQ ID NO: 19 under stringent conditions, and a primer comprising the base sequence shown by SEQ ID NO: 20 or a variant thereof similarly having a function as a primer and comprising a base sequence that hybridizes with the base sequence complementary to the base sequence shown by SEQ ID NO: 20 under stringent conditions,

(11) primer set 11 consisting of a primer comprising the base sequence shown by SEQ ID NO: 21 or a variant thereof similarly having a function as a primer and comprising a base sequence that hybridizes with the base sequence complementary to the base sequence shown by SEQ ID NO: 21 under stringent conditions, and a primer comprising the base sequence shown by SEQ ID NO: 22 or a variant thereof similarly having a function as a primer and comprising a base sequence that hybridizes with the base sequence complementary to the base sequence shown by SEQ ID NO: 22 under stringent conditions,

(12) primer set 12 consisting of a primer comprising the base sequence shown by SEQ ID NO: 23 or a variant thereof similarly having a function as a primer and comprising a base sequence that hybridizes with the base sequence complementary to the base sequence shown by SEQ ID NO: 23 under stringent conditions, and a primer comprising the base sequence shown by SEQ ID NO: 24 or a variant thereof similarly having a function as a primer and comprising a base sequence that hybridizes with the base sequence complementary to the base sequence shown by SEQ ID NO: 24 under stringent conditions,

(13) primer set 13 consisting of a primer comprising the base sequence shown by SEQ ID NO: 25 or a variant thereof similarly having a function as a primer and comprising a base sequence that hybridizes with the base sequence complementary to the base sequence shown by SEQ ID NO: 25 under stringent conditions, and a primer comprising the base sequence shown by SEQ ID NO: 26 or a variant thereof similarly having a function as a primer and comprising a base sequence that hybridizes with the base sequence complementary to the base sequence shown by SEQ ID NO: 26 under stringent conditions,

(14) primer set 14 consisting of a primer comprising the base sequence shown by SEQ ID NO: 27 or a variant thereof similarly having a function as a primer and comprising a base sequence that hybridizes with the base sequence complementary to the base sequence shown by SEQ ID NO: 27 under stringent conditions, and a primer comprising the base sequence shown by SEQ ID NO: 28 or a variant thereof similarly having a function as a primer and comprising a base sequence that hybridizes with the base sequence complementary to the base sequence shown by SEQ ID NO: 28 under stringent conditions,

(15) primer set 15 consisting of a primer comprising the base sequence shown by SEQ ID NO: 29 or a variant thereof similarly having a function as a primer and comprising a base sequence that hybridizes with the base sequence complementary to the base sequence shown by SEQ ID NO: 29 under stringent conditions, and a primer comprising the base sequence shown by SEQ ID NO: 30 or a variant thereof similarly having a function as a primer and comprising a base sequence that hybridizes with the base sequence complementary to the base sequence shown by SEQ ID NO: 30 under stringent conditions,

(16) primer set 16 consisting of a primer comprising the base sequence shown by SEQ ID NO: 31 or a variant thereof similarly having a function as a primer and comprising a base sequence that hybridizes with the base sequence complementary to the base sequence shown by SEQ ID NO: 31 under stringent conditions, and a primer comprising the base sequence shown by SEQ ID NO: 32 or a variant thereof similarly having a function as a primer and comprising a base sequence that hybridizes with the base sequence complementary to the base sequence shown by SEQ ID NO: 32 under stringent conditions,

(17) primer set 17 consisting of a primer comprising the base sequence shown by SEQ ID NO: 33 or a variant thereof similarly having a function as a primer and comprising a base sequence that hybridizes with the base sequence complementary to the base sequence shown by SEQ ID NO: 33 under stringent conditions, and a primer comprising the base sequence shown by SEQ ID NO: 34 or a variant thereof similarly having a function as a primer and comprising a base sequence that hybridizes with the base sequence complementary to the base sequence shown by SEQ ID NO: 34 under stringent conditions,

(18) primer set 18 consisting of a primer comprising the base sequence shown by SEQ ID NO: 35 or a variant thereof similarly having a function as a primer and comprising a base sequence that hybridizes with the base sequence complementary to the base sequence shown by SEQ ID NO: 35 under stringent conditions, and a primer comprising the base sequence shown by SEQ ID NO: 36 or a variant thereof similarly having a function as a primer and comprising a base sequence that hybridizes with the base sequence complementary to the base sequence shown by SEQ ID NO: 36 under stringent conditions,

(19) primer set 19 consisting of a primer comprising the base sequence shown by SEQ ID NO: 37 or a variant thereof similarly having a function as a primer and comprising a base sequence that hybridizes with the base sequence complementary to the base sequence shown by SEQ ID NO: 37 under stringent conditions, and a primer comprising the base sequence shown by SEQ ID NO: 38 or a variant thereof similarly having a function as a primer and comprising a base sequence that hybridizes with the base sequence complementary to the base sequence shown by SEQ ID NO: 38 under stringent conditions,

(20) primer set 20 consisting of a primer comprising the base sequence shown by SEQ ID NO: 39 or a variant thereof similarly having a function as a primer and comprising a base sequence that hybridizes with the base sequence complementary to the base sequence shown by SEQ ID NO: 39 under stringent conditions, and a primer comprising the base sequence shown by SEQ ID NO: 40 or a variant thereof similarly having a function as a primer and comprising a base sequence that hybridizes with the base sequence complementary to the base sequence shown by SEQ ID NO: 40 under stringent conditions,

(21) primer set 21 consisting of a primer comprising the base sequence shown by SEQ ID NO: 41 or a variant thereof similarly having a function as a primer and comprising a base sequence that hybridizes with the base sequence complementary to the base sequence shown by SEQ ID NO: 41 under stringent conditions, and a primer comprising the base sequence shown by SEQ ID NO: 42 or a variant thereof similarly having a function as a primer and comprising a base sequence that hybridizes with the base sequence complementary to the base sequence shown by SEQ ID NO: 42 under stringent conditions,

(22) primer set 22 consisting of a primer comprising the base sequence shown by SEQ ID NO: 43 or a variant thereof similarly having a function as a primer and comprising a base sequence that hybridizes with the base sequence complementary to the base sequence shown by SEQ ID NO: 43 under stringent conditions, and a primer comprising the base sequence shown by SEQ ID NO: 44 or a variant thereof similarly having a function as a primer and comprising a base sequence that hybridizes with the base sequence complementary to the base sequence shown by SEQ ID NO: 44 under stringent conditions, and

(23) primer set 23 consisting of a primer comprising the base sequence shown by SEQ ID NO: 45 or a variant thereof similarly having a function as a primer and comprising a base sequence that hybridizes with the base sequence complementary to the base sequence shown by SEQ ID NO: 45 under stringent conditions, and a primer comprising the base sequence shown by SEQ ID NO: 46 or a variant thereof similarly having a function as a primer and comprising a base sequence that hybridizes with the base sequence complementary to the base sequence shown by SEQ ID NO: 46 under stringent conditions.

The "primer comprising the base sequence shown by SEQ ID NO: 1" and "primer comprising the base sequence shown by SEQ ID NO: 2" in primer set 1 mean the same as the "oligonucleotide comprising the base sequence shown by SEQ ID NO: 1" and "oligonucleotide comprising the base sequence shown by SEQ ID NO: 2", respectively, and are hereinafter also conveniently referred to as "the primer of SEQ ID NO: 1" and "the primer of SEQ ID NO: 2", respectively.

The "variant thereof similarly having a function as a primer and comprising a base sequence that hybridizes with the base sequence complementary to the base sequence shown by SEQ ID NO: 1 under stringent conditions" is an oligonucleotide that hybridizes with the above-mentioned oligonucleotide comprising the base sequence complementary to the base sequence shown by SEQ ID NO: 1 under stringent conditions, and has a function as a primer similar to an oligonucleotide comprising the base sequence shown by SEQ ID NO: 1, i.e., a function capable of PCR amplifying a particular region of HPV6 gene by combining with a primer comprising the base sequence shown by SEQ ID NO: 2. In the following, the variant is also conveniently referred to as "a variant of the primer of SEQ ID NO: 1". Similarly, the "variant thereof similarly having a function as a primer and comprising a base sequence that hybridizes with the base sequence complementary to the base sequence shown by SEQ ID NO: 2 under stringent conditions" is an oligonucleotide that hybridizes with the above-mentioned oligonucleotide comprising the base sequence complementary to the base sequence shown by SEQ ID NO: 2 under stringent conditions, and has a function as a primer similar to an oligonucleotide comprising the base sequence shown by SEQ ID NO: 2, i.e., a function capable of PCR amplifying a particular region of HPV6 gene by combining with a primer comprising the base sequence shown by SEQ ID NO: 1. In the following, it is also conveniently referred to as "a variant of the primer of SEQ ID NO: 2". The "variant" is the original oligonucleotide wherein one or multiple nucleotides are substituted, deleted, inserted or added within the range its function as a primer is maintained.

The stringency in hybridization is known to be a function of temperature, salt concentration, chain length of primer, GC content of nucleotide sequence of primer and concentration of chaotropic agent in hybridization buffer. As the stringent conditions, for example, the conditions described in Sambrook, J. et al. (1998) Molecular Cloning: A Laboratory Manual (2nd ed.), Cold Spring Harbor Laboratory Press, New York, and the like can be used. The stringent temperature condition is about 30° C. or above, more preferably about 37° C. or above, most preferably about 42° C. or above. Other conditions are hybridization time, concentration of detergent (e.g., SDS), presence or absence of carrier DNA and the like, and various stringencies can be set by combining these conditions. Those of ordinary skill in the art can appropriately determine the conditions for obtaining a variant having a function as a PCR primer for amplification of desired HPV gene.

Primer set 1 consists of the "primer of SEQ ID NO: 1" or a "variant of the primer of SEQ ID NO: 1" and the "primer of SEQ ID NO: 2" or the "variant of the primer of SEQ ID NO: 2", and preferably consists of the "primer of SEQ ID NO: 1" and the "primer of SEQ ID NO: 2".

Each primer of primer sets 2 to 23 can be defined in the same manner as primer set 1. To be specific, primer set 2 consists of "the primer of SEQ ID NO: 3" or "a variant of the primer of SEQ ID NO: 3" and "the primer of SEQ ID NO: 4" or "a variant of the primer of SEQ ID NO: 4", preferably "the primer of SEQ ID NO: 3" and "the primer of SEQ ID NO: 4", and can amplify a particular region of HPV11 gene, primer set 3 consists of "the primer of SEQ ID NO: 5" or "a variant of the primer of SEQ ID NO: 5" and "the primer of SEQ ID NO: 6" or "a variant of the primer of SEQ ID NO: 6", preferably "the primer of SEQ ID NO: 5" and "the primer of SEQ ID NO: 6", and can amplify a particular region of HPV16 gene, primer set 4 consists of "the primer of SEQ ID NO: 7" or "a variant of the primer of SEQ ID NO: 7" and "the primer of SEQ ID NO: 8" or "a variant of the primer of SEQ ID NO: 8", preferably "the primer of SEQ ID NO: 7" and "the primer of SEQ ID NO: 8", and can amplify a particular region of HPV18 gene, primer set 5 consists of "the primer of SEQ ID NO: 9" or "a variant of the primer of SEQ ID NO: 9" and "the primer of SEQ ID NO: 10" or "a variant of the primer of SEQ ID NO: 10", preferably "the primer of SEQ ID NO: 9" and "the primer of SEQ ID NO: 10", and can amplify a particular region of HPV30 gene, primer set 6 consists of "the primer of SEQ ID NO: 11" or "a variant of the primer of SEQ ID NO: 11" and "the primer of SEQ ID NO: 12" or "a variant of the primer of SEQ ID NO: 12", preferably "the primer of SEQ ID NO: 11" and "the primer of SEQ ID NO: 12", and can amplify a particular region of HPV31 gene, primer set 7 consists of "the primer of SEQ ID NO: 13" or "a variant of the primer of SEQ ID NO: 13" and "the primer of SEQ ID NO: 14" or "a variant of the primer of SEQ ID NO: 14", preferably "the primer of SEQ ID NO: 13" and "the primer of SEQ ID NO: 14", and can amplify a particular region of HPV33 gene, primer set 8 consists of "the primer of SEQ ID NO: 15" or "a variant of the primer of SEQ ID NO: 15" and "the primer of SEQ ID NO: 16" or "a variant of the primer of SEQ ID NO: 16", preferably "the primer of SEQ ID NO: 15" and "the primer of SEQ ID NO: 16", and can amplify a particular region of HPV34 gene, primer set 9 consists of "the primer of SEQ ID NO: 17" or "a variant of the primer of SEQ ID NO: 17" and "the primer of SEQ ID NO: 18" or "a variant of the primer of SEQ ID NO: 18", preferably "the primer of SEQ ID NO: 17" and "the primer of SEQ ID NO: 18", and can amplify a particular region of HPV35 gene, primer set 10 consists of "the primer of SEQ ID NO: 19" or "a variant of the primer of SEQ ID NO: 19" and "the primer of SEQ ID NO: 20" or "a variant of the primer of SEQ ID NO: 20", preferably "the primer of SEQ ID NO: 19" and "the primer of SEQ ID NO: 20", and can amplify a particular region of HPV39 gene, primer set 11 consists of "the primer of SEQ ID NO: 21" or "a variant of the primer of SEQ ID NO: 21" and "the primer of SEQ ID NO: 22" or "a variant of the primer of SEQ ID NO: 22", preferably "the primer of SEQ ID NO: 21" and "the primer of SEQ ID NO: 22", and can amplify a particular region of HPV40 gene, primer set 12 consists of "the primer of SEQ ID NO: 23" or "a variant of the primer of SEQ ID NO: 23" and "the primer of SEQ ID NO: 24" or "a variant of the primer of SEQ ID NO: 24", preferably "the primer of SEQ ID NO: 23" and "the primer of SEQ ID NO: 24", and can amplify a particular region of HPV42 gene, primer set 13 consists of "the primer of SEQ ID NO: 25" or "a variant of the primer of SEQ ID NO: 25" and "the primer of SEQ ID NO: 26" or "a variant of the primer of SEQ ID NO: 26", preferably "the primer of SEQ ID NO: 25" and "the primer of SEQ ID NO: 26", and can amplify a particular region of HPV45 gene, primer set 14 consists of "the primer of SEQ ID NO: 27" or "a variant of the primer of SEQ ID NO: 27" and "the primer of SEQ ID NO: 28" or "a variant of the primer of SEQ ID NO: 28", preferably "the primer of SEQ ID NO: 27" and "the primer of SEQ ID NO: 28", and can amplify a particular region of HPV51 gene, primer set 15 consists of "the primer of SEQ ID NO: 29" or "a variant of the primer of SEQ ID NO: 29" and "the primer of SEQ ID NO: 30" or "a variant of the primer of SEQ ID NO: 30", preferably "the primer of SEQ ID NO: 29" and "the primer of SEQ ID NO: 30", and can amplify a particular region of HPV52 gene, primer set 16 consists of "the primer of SEQ ID NO: 31" or "a variant of the primer of SEQ ID NO: 31" and "the primer of SEQ ID NO: 32" or "a variant of the primer of SEQ ID NO: 32", preferably "the primer of SEQ ID NO: 31" and "the primer of SEQ ID NO: 32", and can amplify a particular region of HPV53 gene, primer set 17 consists of "the primer of SEQ ID NO: 33" or "a variant of the primer of SEQ ID NO: 33" and "the primer of SEQ ID NO: 34" or "a variant of the primer of SEQ ID NO: 34", preferably "the primer of SEQ ID NO: 33" and "the primer of SEQ ID NO: 34", and can amplify a particular region of HPV54 gene, primer set 18 consists of "the primer of SEQ ID NO: 35" or "a variant of the primer of SEQ ID NO: 35" and "the primer of SEQ ID NO: 36" or "a variant of the primer of SEQ ID NO: 36", preferably "the primer of SEQ ID NO: 35" and "the primer of SEQ ID NO: 36", and can amplify a particular region of HPV56 gene, primer set 19 consists of "the primer of SEQ ID NO: 37" or "a variant of the primer of SEQ ID NO: 37" and "the primer of SEQ ID NO: 38" or "a variant of the primer of SEQ ID NO:

38", preferably "the primer of SEQ ID NO: 37" and "the primer of SEQ ID NO: 38", and can amplify a particular region of HPV58 gene, primer set 20 consists of "the primer of SEQ ID NO: 39" or "a variant of the primer of SEQ ID NO: 39" and "the primer of SEQ ID NO: 40" or "a variant of the primer of SEQ ID NO: 40", preferably "the primer of SEQ ID NO: 39" and "the primer of SEQ ID NO: 40", and can amplify a particular region of HPV59 gene, primer set 21 consists of "the primer of SEQ ID NO: 41" or "a variant of the primer of SEQ ID NO: 41" and "the primer of SEQ ID NO: 42" or "a variant of the primer of SEQ ID NO: 42", preferably "the primer of SEQ ID NO: 41" and "the primer of SEQ ID NO: 42", and can amplify a particular region of HPV61 gene, primer set 22 consists of "the primer of SEQ ID NO: 43" or "a variant of the primer of SEQ ID NO: 43" and "the primer of SEQ ID NO: 44" or "a variant of the primer of SEQ ID NO: 44", preferably "the primer of SEQ ID NO: 43" and "the primer of SEQ ID NO: 44", and can amplify a particular region of HPV66 gene, primer set 23 consists of "the primer of SEQ ID NO: 45" or "a variant of the primer of SEQ ID NO: 45" and "the primer of SEQ ID NO: 46" or "a variant of the primer of SEQ ID NO: 46", preferably "the primer of SEQ ID NO: 45" and "the primer of SEQ ID NO: 46", and can amplify a particular region of HPV68 gene.

One example of each primer set is shown in Table 1. As mentioned later, in the present invention, a primer set for amplifying G3PDH (glyceraldehyde triphosphoric acid dehydrogenase) gene to be utilized as the internal standard can be optionally used. The primer set (primer set 24) for amplifying the G3PDH gene consists of a primer comprising the base sequence shown by SEQ ID NO: 47 or a variant thereof similarly having a function as a primer and comprising a base sequence that hybridizes with the base sequence complementary to the base sequence shown by SEQ ID NO: 47 under stringent conditions, and a primer comprising the base sequence shown by SEQ ID NO: 48 or a variant thereof similarly having a function as a primer and comprising a base sequence that hybridizes with the base sequence complementary to the base sequence shown by SEQ ID NO: 48 under stringent conditions.

TABLE 1

| primer set | virus type | * | primer sequence (5'→3') | SEQ ID NO: | position **(nt) | Tm (° C.) | size of PCR product (bp) |
|---|---|---|---|---|---|---|---|
| 1 | HPV6 | F | TCTGCTGCCCCTAAACGTAAG | 1 | 7251 | 65 | 423 |
|   |       | R | GGTGGAAAGTGTATGCCAAGG | 2 | 7673 | 65 |     |
| 2 | HPV11 | F | CGTTTTCGGTTGCCCTTAC | 3 | 7594 | 64 | 200 |
|   |       | R | ACCTTTGGCTGCAATCCAC | 4 | 7793 | 65 |     |
| 3 | HPV16 | F | CGGTTGCATGCTTTTTGG | 5 | 7458 | 65 | 238 |
|   |       | R | CAGCGGTATGTAAGGCGTTG | 6 | 7695 | 65 |     |
| 4 | HPV18 | F | CTGCACCGGCTGAAAATAAG | 7 | 6910 | 64 | 467 |
|   |       | R | ATAGCCCAACAAGCAACACC | 8 | 7376 | 64 |     |
| 5 | HPV30 | F | ACTAAGGTGCGGTTGTGTCC | 9 | 7324 | 64 | 314 |
|   |       | R | ATAAGGCGAGGCGTCTTACG | 10 | 7637 | 65 |    |
| 6 | HPV31 | F | GGGCGTCTGCAACTACTACTTC | 11 | 5186 | 64 | 276 |
|   |       | R | ACACTTGTGGCGTTGTAGGG | 12 | 5461 | 65 |    |
| 7 | HPV33 | F | GTATTGGCACAGGCTCTGGT | 13 | 4382 | 64 | 476 |
|   |       | R | AATGGGCGTGCTTGATGT | 14 | 4857 | 64 |     |
| 8 | HPV34 | F | CAAGCTGAGCAAGCCTGGTA | 15 | 683 | 65 | 159 |
|   |       | R | TAGGCGTCTGGAACAGTTGG | 16 | 841 | 65 |     |
| 9 | HPV35 | F | CCACTTAGCAGCGTGAGCTT | 17 | 1144 | 64 | 258 |
|   |       | R | GTCTCGCGTTGGAGTCTCAT | 18 | 1401 | 64 |    |
| 10 | HPV39 | F | TAGTTCACGCTGAGCCCTCT | 19 | 5259 | 64 | 432 |
|    |       | R | AGGTGGAGGCAAATACACCA | 20 | 5690 | 64 |    |
| 11 | HPV40 | F | TGCAGTTTGAGCAGCCATC | 21 | 5179 | 65 | 417 |
|    |       | R | CCGTGGCAAGAGGTATGGAT | 22 | 5595 | 66 |    |
| 12 | HPV42 | F | CCCCGTTTGTCCACTACATC | 23 | 5581 | 64 | 228 |
|    |       | R | GCGCCTACGCCAAAAATAAC | 24 | 5808 | 65 |    |
| 13 | HPV45 | F | TAAGCCCCATTGCTGCTACA | 25 | 5203 | 65 | 177 |
|    |       | R | CAGCAGTAGAAGGCATGGTCA | 26 | 5379 | 65 |   |
| 14 | HPV51 | F | GCCATAGTCAGGCAAACGAG | 27 | 1196 | 65 | 381 |
|    |       | R | CTGCTACCATTGGGGAAACG | 28 | 1576 | 66 |    |
| 15 | HPV52 | F | ATAGCACTGCGACGGACCTT | 29 | 767 | 66 | 492 |
|    |       | R | CCGCTGTCTTCTACGTGACAT | 30 | 1258 | 64 |   |
| 16 | HPV53 | F | TACGGTTTTGCAGCAACAGG | 31 | 7820 | 66 | 229 |
|    |       | R | GCAGCTCCAGCAATGGTTTA | 32 | 192 | 65 |    |

TABLE 1-continued

| primer set | virus type | * | primer sequence (5'→3') | SEQ ID NO: | position **(nt) | Tm (° C.) | size of PCR product (bp) |
|---|---|---|---|---|---|---|---|
| 17 | HPV54 | F | ACCAGCCAATACTGCTGCTA | 33 | 3824 | 62 | 349 |
|  |  | R | AGCAGGTTACACAGGGCATC | 34 | 4172 | 64 |  |
| 18 | HPV56 | F | CCGGGAAGGAGTAAAACGG | 35 | 1205 | 65 | 236 |
|  |  | R | CCTGCAATTGTTGTGTTGGC | 36 | 1440 | 66 |  |
| 19 | HPV58 | F | CATTGGTACAGGGTCGGGTA | 37 | 4417 | 64 | 130 |
|  |  | R | ATCCAAAGGCCCCACAGTA | 38 | 4546 | 64 |  |
| 20 | HPV59 | F | GTTTTGCAAAGGGGAACTGC | 39 | 153 | 66 | 364 |
|  |  | R | CGCTTGTCGTTGCTGTCTTA | 40 | 516 | 64 |  |
| 21 | HPV61 | F | CCGTCCTCGTCCCCTAGTATAA | 41 | 5412 | 65 | 185 |
|  |  | R | GATGTCACAGGCGTATCAAGC | 42 | 5596 | 65 |  |
| 22 | HPV66 | F | ATAGGCTGGATGACACTGAGGT | 43 | 6014 | 64 | 233 |
|  |  | R | CACCATGTCACCGTCCTCTATC | 44 | 6246 | 66 |  |
| 23 | HPV68 | F | TGCTACATTTACCTCCCGTTCC | 45 | 1333 | 66 | 383 |
|  |  | R | AATGCCAGTGCGTGTTACG | 46 | 1715 | 65 |  |
| 24 | internal standard G3PDH | F | CAGCCTCAAGATCATCAGCA | 47 | 164 | 64 | 460 |
|  |  | R | AAAGGTGGAGGAGTGGGTGT | 48 | 907 | 65 |  |

*F shows forward primer and R shows reverse primer.
**position (nt) shows the position on genome, to which the 5' terminal of the primer binds.

In the above-mentioned Table 1, the position (nt) on the genome of each virus type and G3PHD, to which each primer binds, is the position in the gene sequence under the accession number in the GenBank (NCBI; National Center for Biotechnology Information) of each gene shown in Table 2.

TABLE 2

| gene name | GenBank accession number |
|---|---|
| HPV6 | AF092932 |
| HPV11 | M14119 |
| HPV16 | NC_001526 |
| HPV18 | X05015 |
| HPV30 | X74474 |
| HPV31 | J04353 |
| HPV33 | M12732 |
| HPV34 | X74476 |
| HPV35 | M74117 |
| HPV39 | M62849 |
| HPV40 | X74478 |
| HPV42 | M73236 |
| HPV45 | X74479 |
| HPV51 | M62877 |
| HPV52 | X74481 |
| HPV53 | X74482 |
| HPV54 | U37488 |
| HPV56 | X74483 |
| HPV58 | D90400 |
| HPV59 | X77858 |
| HPV61 | U31793 |
| HPV66 | U31794 |
| HPV68 | M73258 |
| G3PDH | DQ894744 |

The primer of the present invention is designed to increase specificity to each HPV gene (100% complementarity), not to have a sequence having high homology with other types of HPV, and to show Tm value closer between primer sets. Therefore, when multiplex PCR of a mixture of these is performed in one test tube, a particular type of HPV gene present in a sample can be specifically amplified.

The sequence of the variant of each primer can be designed based on the information of each primer described in Table 1. Specifically, a variant of the primer of SEQ ID NO: 1 is designed to afford a PCR product having the same or higher homology with the PCR product obtained by PCR reaction of the primer of SEQ ID NO: 1 and the primer of SEQ ID NO: 2 by a PCR reaction with the primer of SEQ ID NO: 2 (or a variant of the primer of SEQ ID NO: 2). The level of the homology is not less than 80%, preferably not less than 90%, particularly preferably not less than 95%. The 5' terminal of the primer of SEQ ID NO: 1 binds to the 7251st position on the HPV6 (GenBank accession number: AF092932) genome. A primer that binds to a ±50 position, preferably ±20 position, particularly preferably ±10 position, is also within the scope of the variant of the primer of SEQ ID NO: 1 in the present invention.

The homology (%) can be determined using, as an initial setting, a homology search program (e.g., BLAST, FASTA etc.) conventionally used in the art. In another aspect, the homology (%) can be determined using any algorithm known in the art, for example, algorithm of Needleman et al. (1970) (J. Mol. Biol. 48: 444-453), Myers and Miller (CABIOS, 1988, 4: 11-17) and the like. The algorithm of Needleman et al. has been incorporated into the GAP program of GCG software package (available from www.gcg.com), and the homology (%) can be determined using, for example, BLOSUM 62 matrix or PAM250 matrix, and gap weight: 16, 14, 12, 10, 8, 6 or 4, and length weight: any of 1, 2, 3, 4, 5 or 6. In addition, the algorithm of Myers and Miller is incorporated into ALIGN program, a part of a GCG sequence alignment software package. When the ALIGN program is utilized for comparison of amino acid sequences, for example, PAM120 weight residue table, gap length penalty 12, and gap penalty 4 can be used.

Each nucleotide of the primer set in the present invention can be chemically synthesized using, for example, a general DNA synthesizer (e.g., Model 394 manufactured by Applied Biosystems). Oligonucleotide may be synthesized using any other method well known in the art.

The present invention also provides probe that specifically hybridizes with the aforementioned PCR amplification product. The probe is a single strand DNA contained in the base sequence of each PCR amplification product, and may be either a sense strand DNA or an antisense strand DNA. Specific examples thereof include the following probes (1) to (23).

(1) a probe comprising the base sequence shown by SEQ ID NO: 49 or a variant thereof similarly having a function as a probe and comprising a base sequence that hybridizes with the base sequence complementary to the base sequence shown by SEQ ID NO: 49 under stringent conditions, or a probe comprising the base sequence complementary to the base sequence shown by SEQ ID NO: 49 or a variant thereof similarly having a function as a probe and comprising a base sequence that hybridizes with the base sequence shown by SEQ ID NO: 49 under stringent conditions (probe 1), (2) a probe comprising the base sequence shown by SEQ ID NO: 50 or a variant thereof similarly having a function as a probe and comprising a base sequence that hybridizes with the base sequence complementary to the base sequence shown by SEQ ID NO: 50 under stringent conditions, or a probe comprising the base sequence complementary to the base sequence shown by SEQ ID NO: 50 or a variant thereof similarly having a function as a probe and comprising a base sequence that hybridizes with the base sequence shown by SEQ ID NO: 50 under stringent conditions (probe 2), (3) a probe comprising the base sequence shown by SEQ ID NO: 51 or a variant thereof similarly having a function as a probe and comprising a base sequence that hybridizes with the base sequence complementary to the base sequence shown by SEQ ID NO: 51 under stringent conditions, or a probe comprising the base sequence complementary to the base sequence shown by SEQ ID NO: 51 or a variant thereof similarly having a function as a probe and comprising a base sequence that hybridizes with the base sequence shown by SEQ ID NO: 51 under stringent conditions (probe 3), (4) a probe comprising the base sequence shown by SEQ ID NO: 52 or a variant thereof similarly having a function as a probe and comprising a base sequence that hybridizes with the base sequence complementary to the base sequence shown by SEQ ID NO: 52 under stringent conditions, or a probe comprising the base sequence complementary to the base sequence shown by SEQ ID NO: 52 or a variant thereof similarly having a function as a probe and comprising a base sequence that hybridizes with the base sequence shown by SEQ ID NO: 52 under stringent conditions (probe 4), (5) a probe comprising the base sequence shown by SEQ ID NO: 53 or a variant thereof similarly having a function as a probe and comprising a base sequence that hybridizes with the base sequence complementary to the base sequence shown by SEQ ID NO: 53 under stringent conditions, or a probe comprising the base sequence complementary to the base sequence shown by SEQ ID NO: 53 or a variant thereof similarly having a function as a probe and comprising a base sequence that hybridizes with the base sequence shown by SEQ ID NO: 53 under stringent conditions (probe 5), (6) a probe comprising the base sequence shown by SEQ ID NO: 54 or a variant thereof similarly having a function as a probe and comprising a base sequence that hybridizes with the base sequence complementary to the base sequence shown by SEQ ID NO: 54 under stringent conditions, or a probe comprising the base sequence complementary to the base sequence shown by SEQ ID NO: 54 or a variant thereof similarly having a function as a probe and comprising a base sequence that hybridizes with the base sequence shown by SEQ ID NO: 54 under stringent conditions (probe 6), (7) a probe comprising the base sequence shown by SEQ ID NO: 55 or a variant thereof similarly having a function as a probe and comprising a base sequence that hybridizes with the base sequence complementary to the base sequence shown by SEQ ID NO: 55 under stringent conditions, or a probe comprising the base sequence complementary to the base sequence shown by SEQ ID NO: 55 or a variant thereof similarly having a function as a probe and comprising a base sequence that hybridizes with the base sequence shown by SEQ ID NO: 55 Under stringent conditions (probe 7), (8) a probe comprising the base sequence shown by SEQ ID NO: 56 or a variant thereof similarly having a function as a probe and comprising a base sequence that hybridizes with the base sequence complementary to the base sequence shown by SEQ ID NO: 56 under stringent conditions, or a probe comprising the base sequence complementary to the base sequence shown by SEQ ID NO: 56 or a variant thereof similarly having a function as a probe and comprising a base sequence that hybridizes with the base sequence shown by SEQ ID NO: 56 under stringent conditions (probe 8), (9) a probe comprising the base sequence shown by SEQ ID NO: 57 or a variant thereof similarly having a function as a probe and comprising a base sequence that hybridizes with the base sequence complementary to the base sequence shown by SEQ ID NO: 57 under stringent conditions, or a probe comprising the base sequence complementary to the base sequence shown by SEQ ID NO: 57 or a variant thereof similarly having a function as a probe and comprising a base sequence that hybridizes with the base sequence shown by SEQ ID NO: 57 under stringent conditions (probe 9),

(10) a probe comprising the base sequence shown by SEQ ID NO: 58 or a variant thereof similarly having a function as a probe and comprising a base sequence that hybridizes with the base sequence complementary to the base sequence shown by SEQ ID NO: 58 under stringent conditions, or a probe comprising the base sequence complementary to the base sequence shown by SEQ ID NO: 58 or a variant thereof similarly having a function as a probe and comprising a base sequence that hybridizes with the base sequence shown by SEQ ID NO: 58 under stringent conditions (probe 10),

(11) a probe comprising the base sequence shown by SEQ ID NO: 59 or a variant thereof similarly having a function as a probe and comprising a base sequence that hybridizes with the base sequence complementary to the base sequence shown by SEQ ID NO: 59 under stringent conditions, or a probe comprising the base sequence complementary to the base sequence shown by SEQ ID NO: 59 or a variant thereof similarly having a function as a probe and comprising a base sequence that hybridizes with the base sequence shown by SEQ ID NO: 59 under stringent conditions (probe 11),

(12) a probe comprising the base sequence shown by SEQ ID NO: 60 or a variant thereof similarly having a function as a probe and comprising a base sequence that hybridizes with the base sequence complementary to the base sequence shown by SEQ ID NO: 60 under stringent conditions, or a probe comprising the base sequence complementary to the base sequence shown by SEQ ID NO: 60 or a variant thereof similarly having a function as a probe and comprising a base sequence that hybridizes with the base sequence shown by SEQ ID NO: 60 under stringent conditions (probe 12),

(13) a probe comprising the base sequence shown by SEQ ID NO: 61 or a variant thereof similarly having a function as a probe and comprising a base sequence that hybridizes with the base sequence complementary to the base sequence shown by SEQ ID NO: 61 under stringent conditions, or a probe comprising the base sequence complementary to the base sequence shown by SEQ ID NO: 61 or a variant thereof similarly having a function as a probe and comprising a base sequence that hybridizes with the base sequence shown by SEQ ID NO: 61 under stringent conditions (probe 13),

(14) a probe comprising the base sequence shown by SEQ ID NO: 62 or a variant thereof similarly having a function as a probe and comprising a base sequence that hybridizes with the base sequence complementary to the base sequence shown by SEQ ID NO: 62 under stringent conditions, or a probe comprising the base sequence complementary to the base sequence shown by SEQ ID NO: 62 or a variant thereof similarly having a function as a probe and comprising a base sequence that hybridizes with the base sequence shown by SEQ ID NO: 62 under stringent conditions (probe 14),

(15) a probe comprising the base sequence shown by SEQ ID NO: 63 or a variant thereof similarly having a function as a probe and comprising a base sequence that hybridizes with the base sequence complementary to the base sequence shown by SEQ ID NO: 63 under stringent conditions, or a probe comprising the base sequence complementary to the base sequence shown by SEQ ID NO: 63 or a variant thereof similarly having a function as a probe and comprising a base sequence that hybridizes with the base sequence shown by SEQ ID NO: 63 under stringent conditions (probe 15),

(16) a probe comprising the base sequence shown by SEQ ID NO: 64 or a variant thereof similarly having a function as a probe and comprising a base sequence that hybridizes with the base sequence complementary to the base sequence shown by SEQ ID NO: 64 under stringent conditions, or a probe comprising the base sequence complementary to the base sequence shown by SEQ ID NO: 64 or a variant thereof similarly having a function as a probe and comprising a base sequence that hybridizes with the base sequence shown by SEQ ID NO: 64 under stringent conditions (probe 16),

(17) a probe comprising the base sequence shown by SEQ ID NO: 65 or a variant thereof similarly having a function as a probe and comprising a base sequence that hybridizes with the base sequence complementary to the base sequence shown by SEQ ID NO: 65 under stringent conditions, or a probe comprising the base sequence complementary to the base sequence shown by SEQ ID NO: 65 or a variant thereof similarly having a function as a probe and comprising a base sequence that hybridizes with the base sequence shown by SEQ ID NO: 65 under stringent conditions (probe 17),

(18) a probe comprising the base sequence shown by SEQ ID NO: 66 or a variant thereof similarly having a function as a probe and comprising a base sequence that hybridizes with the base sequence complementary to the base sequence shown by SEQ ID NO: 66 under stringent conditions, or a probe comprising the base sequence complementary to the base sequence shown by SEQ ID NO: 66 or a variant thereof similarly having a function as a probe and comprising a base sequence that hybridizes with the base sequence shown by SEQ ID NO: 66 under stringent conditions (probe 18),

(19) a probe comprising the base sequence shown by SEQ ID NO: 67 or a variant thereof similarly having a function as a probe and comprising a base sequence that hybridizes with the base sequence complementary to the base sequence shown by SEQ ID NO: 67 under stringent conditions, or a probe comprising the base sequence complementary to the base sequence shown by SEQ ID NO: 67 or a variant thereof similarly having a function as a probe and comprising a base sequence that hybridizes with the base sequence shown by SEQ ID NO: 67 under stringent conditions (probe 19),

(20) a probe comprising the base sequence shown by SEQ ID NO: 68 or a variant thereof similarly having a function as a probe and comprising a base sequence that hybridizes with the base sequence complementary to the base sequence shown by SEQ ID NO: 68 under stringent conditions, or a probe comprising the base sequence complementary to the base sequence shown by SEQ ID NO: 68 or a variant thereof similarly having a function as a probe and comprising a base sequence that hybridizes with the base sequence shown by SEQ ID NO: 68 under stringent conditions (probe 20),

(21) a probe comprising the base sequence shown by SEQ ID NO: 69 or a variant thereof similarly having a function as a probe and comprising a base sequence that hybridizes with the base sequence complementary to the base sequence shown by SEQ ID NO: 69 under stringent conditions, or a probe comprising the base sequence complementary to the base sequence shown by SEQ ID NO: 69 or a variant thereof similarly having a function as a probe and comprising a base sequence that hybridizes with the base sequence shown by SEQ ID NO: 69 under stringent conditions (probe 21),

(22) a probe comprising the base sequence shown by SEQ ID NO: 70 or a variant thereof similarly having a function as a probe and comprising a base sequence that hybridizes with the base sequence complementary to the base sequence shown by SEQ ID NO: 70 under stringent conditions, or a probe comprising the base sequence complementary to the base sequence shown by SEQ ID NO: 70 or a variant thereof similarly having a function as a probe and comprising a base sequence that hybridizes with the base sequence shown by SEQ ID NO: 70 under stringent conditions (probe 22), and

(23) a probe comprising the base sequence shown by SEQ ID NO: 71 or a variant thereof similarly having a function as a probe and comprising a base sequence that hybridizes with the base sequence complementary to the base sequence shown by SEQ ID NO: 71 under stringent conditions, or a probe comprising the base sequence complementary to the base sequence shown by SEQ ID NO: 71 or a variant thereof similarly having a function as a probe and comprising a base sequence that hybridizes with the base sequence shown by SEQ ID NO: 71 under stringent conditions (probe 23).

The "probe comprising the base sequence shown by SEQ ID NO: 49" in probe 1 means the same as the "oligonucleotide comprising the base sequence shown by SEQ ID NO: 49", and is hereinafter also conveniently referred to as "the probe of SEQ ID NO: 49".

The "variant thereof similarly having a function as a probe and comprising a base sequence that hybridizes with the base sequence complementary to the base sequence shown by SEQ ID NO: 49 under stringent conditions" is an oligonucleotide that hybridizes with the above-mentioned oligonucleotide comprising the base sequence complementary to the base sequence shown by SEQ ID NO: 49 under stringent conditions, and has a function as a probe similar to an oligonucleotide comprising the base sequence shown by SEQ ID NO: 49, i.e., a function capable of detecting a particular region of HPV6 gene. In the following, the variant is also conveniently referred to as "a variant of the probe of SEQ ID NO: 49". The "variant" is the original oligonucleotide wherein one or multiple nucleotides are substituted, deleted, inserted or added within the range its function as a probe is maintained.

The "probe comprising the base sequence complementary to the base sequence shown by SEQ ID NO: 49" means the same as an "oligonucleotide comprising the base sequence complementary to the base sequence shown by SEQ ID NO: 49", and is hereinafter also conveniently referred to as "the probe complementary to SEQ ID NO: 49".

The "variant thereof similarly having a function as a probe and comprising a base sequence that hybridizes with the base sequence shown by SEQ ID NO: 49 under stringent conditions" is an oligonucleotide which hybridizes with the above-mentioned oligonucleotide comprising the base sequence shown by SEQ ID NO: 49 under stringent conditions, and has a function as a probe similar to an oligonucleotide comprising the base sequence complementary to the base sequence shown by SEQ ID NO: 49, i.e., a function capable of detecting a particular region of HPV6 gene. In the following, the variant is also conveniently referred to as "a variant of the probe complementary to SEQ ID NO: 49". The "variant" is the original oligonucleotide wherein one or multiple nucleotides are substituted, deleted, inserted or added within the range its function as a probe is maintained.

The stringency in hybridization is known to be a function of temperature, salt concentration, chain length of probe, GC content of nucleotide sequence of probe and concentration of chaotropic agent in hybridization buffer. As the stringent conditions, for example, the conditions described in Sambrook, J. et al. (1998) Molecular Cloning: A Laboratory Manual (2nd ed.), Cold Spring Harbor Laboratory Press, New York, and the like can be used. The stringent temperature condition is about 30° C. or above, more preferably about 37° C. or above, most preferably about 42° C. or above. Other conditions are hybridization time, concentration of detergent (e.g., SDS), presence or absence of carrier DNA and the like, and various stringencies can be set by combining these conditions. Those of ordinary skill in the art can appropriately determine the conditions for obtaining a variant having a function as a probe for detection of desired HPV gene.

Probe 1 is any of "the probe of SEQ ID NO: 49", "a variant of the probe of SEQ ID NO: 49", "the probe complementary to SEQ ID NO: 49" and "a variant of the probe complementary to SEQ ID NO: 49", preferably "the probe of SEQ ID NO: 49" or "the probe complementary to SEQ ID NO: 49".

Probes 2 to 23 can be defined in the same manner as probe 1. To be specific, probe 2 is any of "the probe of SEQ ID NO: 50", "a variant of the probe of SEQ ID NO: 50", "the probe complementary to SEQ ID NO: 50" and "a variant of the probe complementary to SEQ ID NO: 50", preferably "the probe of SEQ ID NO: 50" or "the probe complementary to SEQ ID NO: 50", and can detect a particular region of HPV11 gene, probe 3 is any of "the probe of SEQ ID NO: 51", "a variant of the probe of SEQ ID NO: 51", "the probe complementary to SEQ ID NO: 51" and "a variant of the probe complementary to SEQ ID NO: 51", preferably "the probe of SEQ ID NO: 51" or "the probe complementary to SEQ ID NO: 51", and can detect a particular region of HPV16 gene, probe 4 is any of "the probe of SEQ ID NO: 52", "a variant of the probe of SEQ ID NO: 52", "the probe complementary to SEQ ID NO: 52" and "a variant of the probe complementary to SEQ ID NO: 52", preferably "the probe of SEQ ID NO: 52" or "the probe complementary to SEQ ID NO: 52", and can detect a particular region of HPV18 gene, probe 5 is any of "the probe of SEQ ID NO: 53", "a variant of the probe of SEQ ID NO: 53", "the probe complementary to SEQ ID NO: 53" and "a variant of the probe complementary to SEQ ID NO: 53", preferably "the probe of SEQ ID NO: 53" or "the probe complementary to SEQ ID NO: 53", and can detect a particular region of HPV30 gene, probe 6 is any of "the probe of SEQ ID NO: 54", "a variant of the probe of SEQ ID NO: 54", "the probe complementary to SEQ ID NO: 54" and "a variant of the probe complementary to SEQ ID NO: 54", preferably "the probe of SEQ ID NO: 54" or "the probe complementary to SEQ ID NO: 54", and can detect a particular region of HPV31 gene, probe 7 is any of "the probe of SEQ ID NO: 55", "a variant of the probe of SEQ ID NO: 55", "the probe complementary to SEQ ID NO: 55" and "a variant of the probe complementary to SEQ ID NO: 55", preferably "the probe of SEQ ID NO: 55" or "the probe complementary to SEQ ID NO: 55", and can detect a particular region of HPV33 gene, probe 8 is any of "the probe of SEQ ID NO: 56", "a variant of the probe of SEQ ID NO: 56", "the probe complementary to SEQ ID NO: 56" and "a variant of the probe complementary to SEQ ID NO: 56", preferably "the probe of SEQ ID NO: 56" or "the probe complementary to SEQ ID NO: 56", and can detect a particular region of HPV34 gene, probe 9 is any of "the probe of SEQ ID NO: 57", "a variant of the probe of SEQ ID NO: 57", "the probe complementary to SEQ ID NO: 57" and "a variant of the probe complementary to SEQ ID NO: 57", preferably "the probe of SEQ ID NO: 57" or "the probe complementary to SEQ ID NO: 57", and can detect a particular region of HPV35 gene, probe 10 is any of "the probe of SEQ ID NO: 58", "a variant of the probe of SEQ ID NO: 58", "the probe complementary to SEQ ID NO: 58" and "a variant of the probe complementary to SEQ ID NO: 58", preferably "the probe of SEQ ID NO: 58" or "the probe complementary to SEQ ID NO: 58", and can detect a particular region of HPV39 gene, probe 11 is any of "the probe of SEQ ID NO: 59", "a variant of the probe of SEQ ID NO: 59", "the probe complementary to SEQ ID NO: 59" and "a variant of the probe complementary to SEQ ID NO: 59", preferably "the probe of SEQ ID NO: 59" or "the probe complementary to SEQ ID NO: 59", and can detect a particular region of HPV40 gene, probe 12 is any of "the probe of SEQ ID NO: 60", "a variant of the probe of SEQ ID NO: 60", "the probe complementary to SEQ ID NO: 60" and "a variant of the probe complementary to SEQ ID NO: 60", preferably "the probe of SEQ ID NO: 60" or "the probe complementary to SEQ ID NO: 60", and can detect a particular region of HPV42 gene, probe 13 is any of "the probe of SEQ ID NO: 61", "a variant of the probe of SEQ ID NO: 61", "the probe complementary to SEQ ID NO: 61" and "a variant of the probe complementary to SEQ ID NO: 61", preferably "the probe of SEQ ID NO: 61" or "the probe complementary to SEQ ID NO: 61", and can detect a particular region of HPV45 gene, probe 14 is any of "the probe of SEQ ID NO: 62", "a variant of the probe of SEQ ID NO: 62", "the probe complementary to SEQ ID NO: 62" and "a variant of the probe complementary to SEQ ID NO: 62", preferably "the probe of SEQ ID NO: 62" or "the probe complementary to SEQ ID NO: 62", and can detect a particular region of HPV51 gene, probe 15 is any of "the probe of SEQ ID NO: 63", "a variant of the probe of SEQ ID NO: 63", "the probe complementary to SEQ ID NO: 63" and "a variant of the probe complementary to SEQ ID NO: 63", preferably "the probe of SEQ ID NO: 63" or "the probe complementary to SEQ ID NO: 63", and can detect a particular region of HPV52 gene, probe 16 is any of "the probe of SEQ ID NO: 64", "a variant of the probe of SEQ ID NO: 64", "the probe complementary to SEQ ID NO: 64" and "a variant of the probe complementary to SEQ ID NO: 64", preferably "the probe of SEQ ID NO: 64" or "the probe complementary to SEQ ID NO: 64", and can detect a particular region of HPV53 gene, probe 17 is any of "the probe of SEQ ID NO: 65", "a variant of the probe of SEQ ID NO: 65", "the probe complementary to SEQ ID NO: 65" and "a variant of the probe complementary to SEQ ID NO: 65", preferably "the probe of SEQ ID NO: 65" or "the probe complementary to SEQ ID NO: 65", and can detect a particular region of HPV54 gene, probe 18 is any of "the probe of SEQ ID NO: 66", "a variant of the probe of SEQ ID NO: 66", "the probe complementary to SEQ ID NO: 66" and "a variant of the probe complementary to SEQ ID NO: 66", preferably "the probe of SEQ ID NO: 66" or "the probe complementary to SEQ ID NO: 66", and can detect a particular region of HPV56 gene, probe 19 is any of "the probe of SEQ ID NO: 67", "a variant of the probe of SEQ ID NO: 67", "the probe complementary to SEQ ID NO: 67" and "a variant of the probe complementary to SEQ ID NO: 67", preferably "the probe of SEQ ID NO: 67" or "the probe complementary to SEQ ID NO: 67", and can detect a particular region of HPV58 gene, probe 20 is any of "the probe of SEQ ID NO: 68", "a variant of the probe of SEQ ID NO: 68", "the probe complementary to SEQ ID NO: 68" and "a variant of the probe complementary to SEQ ID NO: 68", preferably "the probe of SEQ ID NO: 68" or "the probe complementary to SEQ ID NO: 68", and can detect a particular region of HPV59 gene, probe 21 is any of "the probe of SEQ ID NO: 69", "a variant of the probe of SEQ ID NO: 69", "the probe complementary to SEQ ID NO: 69" and "a variant of the probe complementary to SEQ ID NO: 69", preferably "the probe of SEQ ID NO: 69" or "the probe complementary to SEQ ID NO: 69", and can detect a particular region of HPV61 gene, probe 22 is any of "the probe of SEQ ID NO: 70", "a variant of the probe of SEQ ID NO: 70", "the probe complementary to SEQ ID NO: 70" and "a variant of the probe complementary to SEQ ID NO: 70", preferably "the probe of SEQ ID NO: 70" or "the probe complementary to SEQ ID NO: 70", and can detect a particular region of HPV66 gene, probe 23 is any of "the probe of SEQ ID NO: 71", "a variant of the probe of SEQ ID NO: 71", "the probe complementary to SEQ ID NO: 71" and "a variant of the probe complementary to SEQ ID NO: 71", preferably "the probe of SEQ ID NO: 71" or "the probe complementary to SEQ ID NO: 71", and can detect a particular region of HPV68 gene.

One example of each probe when it is sense strand DNA is shown in Table 3. As mentioned later, in the present invention, a probe for detecting G3PDH gene to be utilized as the internal standard can be optionally used. The probe (probe 24) for detecting the G3PDH gene is a probe comprising the base sequence shown by SEQ ID NO: 72 or a variant thereof similarly having a function as a probe and comprising a base sequence that hybridizes with the base sequence complementary to the base sequence shown by SEQ ID NO: 72 under stringent conditions, or a probe comprising the base sequence complementary to the base sequence shown by SEQ ID NO: 72 or a variant thereof similarly having a function as a probe and comprising a base sequence that hybridizes with the base sequence shown by SEQ ID NO: 72 under stringent conditions.

The base sequence, Tm value, size and position on genome of each probe are shown in Table 3.

TABLE 3

| probe No. | virus type | sequence | SEQ ID NO: | Tm (° C.) | size (bp) | position (nt) | |
|---|---|---|---|---|---|---|---|
| 1 | HPV6 | CACCCTGTGACTCAGTGGCTGTTGCACGCGTTTTGGTTTG CACGCGCCTTACACACATAAGTAATATACA | 49 | 75 | 70 | 7519 | 7588 |
| 2 | HPV11 | GCCCTGCCAAGTATCTTGCCAACAACACACCTGGCCAGGG CGCGGTATTGCATGACTAATGTACAATAAA | 50 | 76 | 70 | 7684 | 7753 |
| 3 | HPV16 | CGTTTCCTGCTTGCCATGCGTGCCAAATCCCTGTTTTCCT GACCTGCACTGCTTGCCAACCATTCCATTG | 51 | 77 | 70 | 7532 | 7601 |
| 4 | HPV18 | ATTGCGTCGCAAGCCCACCATAGGCCCTCGCAAACGTTCT GCTCCATCTGCCACTACGTCTTCTAAACCT | 52 | 78 | 70 | 7034 | 7103 |
| 5 | HPV30 | GGCATTTAGGTAGCAATTTAGGTGGCGTCCCTATGTCCTC CACCCTTTTTGGTTGTTGCACACCACTGTG | 53 | 76 | 70 | 7347 | 7416 |
| 6 | HPV31 | CACCCTGCCACACATAATGTTTCCCCTTCTACTGCTGTACA GTCCACATCTGCTGTGTCTGCCTATGTACC | 54 | 76 | 70 | 5264 | 5333 |
| 7 | HPV33 | ACCTATTGGTACTGACCCACCTACAGCTGCAATCCCCTTG CAGCCTATACGTCCTCCGGTTACTGTAGAC | 55 | 77 | 70 | 4425 | 4494 |
| 8 | HPV34 | GCAGCAGATGTCAGTCCACAGTGTGTCTTACCATTGAGAG CACACACGCTGACCTATTAGTGTTAGAAGA | 56 | 75 | 70 | 720 | 789 |
| 9 | HPV35 | CAGGTAGAGGGGCATGATACAGTTGAACAATGTAGTATGG GCAGTGGGGATAGTATAACCTCTAGTAGCG | 57 | 75 | 70 | 1300 | 1369 |
| 10 | HPV39 | GGGATTCGGGCACTACATATAACACAGGCTCACTACCTTC TGTGGCTTCTTCAGCATCTACTAAATATGCC | 58 | 74 | 71 | 5358 | 5428 |

TABLE 3-continued

| probe No. | virus type | sequence | SEQ ID NO: | Tm (° C.) | size (bp) | position (nt) |
|---|---|---|---|---|---|---|
| 11 | HPV40 | CGGCACCACATACACTGGAGACACCACATACACTAGAGAC ACCACTGGACACTACTGATGCCCTGTTTGA | 59 | 76 | 70 | 6416 5485 |
| 12 | HPV42 | ACTGTGCATGTGGGCCCTGATTTATCTGTTGTGGACCACC CATGGGACAGTACCCCAACGTCTGTAATGC | 60 | 77 | 70 | 5668 5737 |
| 13 | HPV45 | GTGCTACAAATGATAGTGACCTGTTTGATGTATATGCAGA CTTCCCACCTCCTGCGTCCACTACACCTAG | 61 | 75 | 70 | 5251 5320 |
| 14 | HPV51 | GATGGGCAACATGGCGGTTCACAGAACAGTGTGTGTAGTA GCGGGGGGGGCAGTGTTATGGATGTGGAAA | 62 | 78 | 70 | 1306 1375 |
| 15 | HPV52 | CAAGCAGTCCGGAAAGTGCTGGGCAAGATGGTGTAGAAAA ACATGGTAGTCCGCGTGCAAAACACATTTG | 63 | 75 | 70 | 1132 1201 |
| 16 | HPV53 | CACCCAGGACATCCATGGATCGTCAGTTATTTGAAAATAC AGAAGAGCGACCACGTACATTGCACCAGC | 64 | 75 | 69 | 88 156 |
| 17 | HPV54 | GTGTATATAGTGAGGTATGTATGGTGAGTATGGTAGTGAG TGCATGCAGGCCTGCAGTGACTGAGGTGAG | 65 | 75 | 70 | 3845 3914 |
| 18 | HPV56 | GAGGTACAGGGACGTGGGTGCGGGAATACACAAAATGGAG GCTCACAAAACAGTACCTATAGTAACAATA | 66 | 74 | 70 | 1305 1374 |
| 19 | HPV58 | ATATGTGCCCCTTGGTAGTACCCCACCGTCTGAGGCTATA CCTTTACAGCCCATACGTCCCCCAGTTACC | 67 | 78 | 70 | 4453 4522 |
| 20 | HPV59 | GAGGCTGAAACCAAGACACCGTTACATGAGCTGCTGATAC GCTGTTATAGATGCCTAAAACCTCTATGTCC | 68 | 74 | 71 | 325 395 |
| 21 | HPV61 | TATGCTGACCCTGAGGTGTTGGATCTTCCTGCACAACATA CACAACCCACACTTACAGTACAGGGCCCTT | 69 | 76 | 70 | 5445 5514 |
| 22 | HPV66 | GCACCAGCATTAGGGGAACATTGGACTAAGGGCGCGGTGT GTAAGTCTACACCAGGTAATACAGGGGATT | 70 | 76 | 70 | 6127 6196 |
| 23 | HPV68 | TGTTGTGTTACCAGCAACGTCTCCACAGTTGCCTTTAACA CCCTCTACACCAATTGATACAACCTATGCC | 71 | 74 | 70 | 1459 1528 |
| 24 | G3PDH | AAACCTGCCAAATATGATGACATCAAGAAGGTGGTGAAGC AGGCGTCGGAGGGCCCCCTCAAGGGCATCC | 72 | 78 | 70 | 773 842 |

The position (nt) is shown by the position (5'→3') on the genome of each virus type and G3PDH, of the probe, a sense strand DNA. The position corresponds to that in the gene sequence under the GenBank accession number of each gene shown in Table 2.

The probe has a comparatively short length of 69-71 bp, and is designed not to have a sequence having high homology with other types of HPV. Therefore, it hybridizes with each PCR amplification product with extremely high specificity. For example, the presence or absence of each HPV in a sample can be detected by hybridizing a PCR amplification product with DNA microarray for the detection wherein a probe specific to each HPV is immobilized on a support.

The sequence of the variant of each probe can be designed based on the information of each probe described in Table 3. To be specific, a variant of the probe of SEQ ID NO: 49 is designed to be an oligonucleotide having high homology permitting hybridization with an oligonucleotide comprising the base sequence complementary to the 7519th-7588th base sequence on HPV6 genome under stringent conditions. The level of the homology is not less than 80%, preferably not less than 90%, particularly preferably not less than 95%. The probe of SEQ ID NO: 49 corresponds to the 7519th-7588th region on HPV6 (GenBank accession number: AF092932) genome. As long as the HPV6 gene can be specifically detected, the 5' terminal side and the 3' terminal side may be shifted by ±50 positions, preferably ±20 positions, particularly preferably ±10 positions.

When the probe is antisense strand DNA, a desired HPV type-specific probe can be designed based on the sequence complementary to each HPV gene specific sequence as described in Table 3.

The homology (%) can be determined using, as an initial setting, a homology search program (e.g., BLAST, FASTA etc.) conventionally used in the art. In another aspect, the homology (%) can be determined using any algorithm known in the art, for example, algorithm of Needleman et al. (1970) (J. Mol. Biol. 48: 444-453), Myers and Miller (CABIOS, 1988, 4: 11-17) and the like. The algorithm of Needleman et al. has been incorporated into the GAP program of GCG software package (available from www.gcg.com), and the homology (%) can be determined using, for example, BLOSUM 62 matrix or PAM250 matrix, and gap weight: 16, 14, 12, 10, 8, 6 or 4, and length weight: any of 1, 2, 3, 4, 5 or 6. In addition, the algorithm of Myers and Miller are incorporated into ALIGN program, a part of a GCG sequence alignment software package. When the ALIGN program is utilized for comparison of amino acid sequences, for example, PAM120 weight residue table, gap length penalty 12, and gap penalty 4 can be used.

Each nucleotide of the probes can be chemically synthesized using, for example, a general DNA synthesizer (e.g., Model 394 manufactured by Applied Biosystems). Oligonucleotide may be synthesized using any other method well known in the art.

In one aspect of the present invention, a kit for HPV detection is provided, which comprises one or more, preferably two or more, combinations of an HPV type-specific primer set and a probe. Detection of HPV using the kit includes PCR using a type-specific primer set to amplify HPV gene of the corresponding type, and detection of the presence of HPV using a probe that specifically hybridizes with each amplification product. The primer sets of the present invention are designed to show approximate Tm values, and therefore, are particularly preferable for multiplex PCR reaction using a mixture of multiple primer sets.

The PCR amplification products obtained by primer sets 1-23 are each detected type-specifically by probes 1-23. For example, when primer set 1 is used, probe 1 is used for the detection of the PCR amplification product thereof.

For detection of HPV using the kit of the present invention, DNA in a sample is extracted, and the DNA is subjected to PCR using the aforementioned primer set. As the sample, tissue sample, biopsy, smear and the like obtained from a test subject suspected to be infected with HPV can be used. Furthermore, cervical squamous cells generally infected with HPV may be concentrated from the collected cells by density gradient centrifugation operation and used. Alternatively, cultured cells, such as HeLa cell and the like may be used. Target diseases for which detection of the presence of HPV gene according to the present invention is considered useful includes wart, intraepithelial neoplasm, skin cancer, mouth cavity/oropharyngeal cancer, genital neoplasm, cervical cancer, condyloma, papilloma and the like.

A method of extracting DNA from a sample is well known in the art and, for example, extraction with phenol and chloroform, or extraction using a commercially available DNA extraction reagent can be performed. Alternatively, extraction may be performed using a column kit (GENERATION (registered trade mark) Capture Column Kit Gentra).

Using DNA thus-extracted from the sample as a template, PCR is performed using the aforementioned primer set to amplify each type of HPV gene. The method of PCR itself is well known in the art (Saiki et al., Science, 239: 487-491, 1988), and is performed using a primer hybridizing to a sense strand (reverse primer) and a primer hybridizing to an antisense strand (forward primer) by repeating a cycle of annealing, elongation and denaturation steps about 20 times to 40 times in the presence of these primers, template DNA (i.e., HPV gene) and heat-resistant DNA polymerase. In the HPV detection using the kit of the present invention, for example, FastStart Taq DNA Polymerase (Roche), Ex Taq (registered trade mark, Takara), Z-Taq, AccuPrime Taq DNA Polymerase, polymerase contained in M-PCR kit (QIAGEN) and the like can be used as the aforementioned DNA polymerase. A method of selecting suitable PCR reaction conditions based on the Tm value of primer is well known in the art, and those of ordinary skill in the art can select optimal conditions based on the length of primer, GC content, objective specificity and sensitivity, property of polymerase to be used, and the like. For example, in the following Examples, PCR was performed by 30 cycles of 95° C. for 4 min, then 95° C. for 30 sec, 60° C. for 30 sec and 72° C. for 1 min, and then 72° C. for 7 min. In addition, the amount of the primer contained in the PCR solution can be appropriately adjusted to achieve desired detection sensitivity and decrease variation in the detection sensitivity depending on virus types.

The DNA product amplified by PCR is subjected to a hybridization reaction using the probe of the present invention capable of detecting HPV in a corresponding type-specific manner. The hybridization can be performed conveniently and with high accuracy by, for example, using labeling probe and microarray. As a hybridization method using a labeled DNA probe, specifically, for example, known methods such as Allele-specific Oligonucleotide Probe method, Oligonucleotide Ligation Assay method, Invader method and the like can be employed. In addition, diagnosis by microarray can be performed, for example, as in the following. To be specific, DNA isolated from a biological sample (for example, blood etc.) of a test subject is amplified by PCR (DNA amplification product) using each type-specific primer set. On that occasion, a labeled dNTP is incorporated to give a labeled DNA. The labeled DNA is contacted with microarray, and DNA that hybridized with a probe immobilized in advance on the microarray is detected. The hybridization can be performed by dispensing an aqueous solution of the labeled DNA to a 0.2 ml or 1.5 ml plastic tube, and spot dropping the solution on the microarray. The amount of the spot drop can be about 5-100 µl. The hybridization is preferably performed within the temperature range of room temperature −70° C. for 0.5-20 hr. After the completion of the hybridization, unreacted labeled DNA is removed by washing with a mixed solution of a surfactant and a buffer. As the surfactant, sodium dodecylsulfate (SDS) or polyethylene 20 sorbitan monolaurate (Tween 20) is preferably used. As the buffer, citrate buffer, phosphate buffer, borate buffer, tris buffer, Good's buffer and the like can be used, with preference given to citrate buffer.

As a method for simultaneously hybridizing multiple DNA amplification products with probe biopolymers, for example, the method described in JP-B-3860174 can be used.

The present invention provides a DNA microarray for detection of HPV, wherein at least one kind, preferably 2 or more, selected from the group consisting of probes 1-23 are immobilized. The DNA microarray may contain probe 24 immobilized as an internal standard.

As a preparation method of a microarray, a method including directly synthesizing oligonucleotide on a support surface (on-chip method), and a method including fixing oligonucleotide prepared in advance on a support surface are known. While the microarray of the present invention can be produced according to any of these methods, a convenient method is the latter. As the on-chip method, a method including selective synthesis in a given region of a small matrix by combining use of a protecting group that can be selectively removed by light irradiation, and a photolithography technique utilized for semiconductor production and a solid phase synthesis technique (masking technique: e.g., Fodor, S. P. A. Science 251: 767, 1991) and the like can be performed. On the other hand, when an oligonucleotide prepared in advance is immobilized on a solid phase carrier surface, the oligonucleotide is spot dropped on the surface of a surface-treated support, and ion-bonded or Covalent-bonded (e.g., Lamture, J. B. et al. Nucl. Acids Res. 22: 2121-2125, 1994; Guo, Z. et al. Nucl. Acids Res. 22: 5456-5465, 1994). Oligonucleotide is generally covalent-bonded on a surface-treated support via a spacer or crosslinker. A method including aligning small pieces of polyacrylamide gel on a glass surface, and covalent-bonding synthetic oligonucleotide thereto is also known (Yershov, G. et al. Proc. Natl. Acad. Sci. USA 94:4913, 1996).

In addition, a glass surface coated with poly-L-lysine or aminopropylsilane can also be used as a support. Examples of the support include nylon membrane, nitrocellulose membrane, glass, silicon chip and the like. Furthermore, a probe can be immobilized by any method utilized in the art, and generally, DNA may be immobilized on a support using a spotter and the like.

When a DNA microarray is used for detection of HPV using the kit of the present invention, amplified DNA products are preferably labeled in advance before subjecting to hybridization, and labeling during amplification is particularly preferable. Examples of the labeling method include two methods: a method including preparing, for production of PCR amplification product, 4 kinds of deoxynucleotides ATCG (dATP, dCTP, dGTP, dTTP: collectively dNTP) and labeled deoxynucleotides (e.g., Cy3-dUTP) to be the substrates of DNA polymerase enzyme to adjust the final concentration of each dNTP to the same level, and allowing incorporation of the labeled deoxynucleotide into the amplification product to be prepared, and a method including PCR reaction using a primer labeled in advance to label DNA.

A labeling substance preferably contains any one of a fluorescent substance and biotin, from the aspects of detection sensitivity and convenient of labeling. Preferable examples of the fluorescent substance include FITC, FAM, Cy3, Cy5, Cy5.5, Cy7, TAMRA, Dabcyl, ROX, TET, Rhodamine, Texas Red, HEX, Cyber Green and the like, and a particularly preferable fluorescent substance is Cy3. In the case of biotin and digoxygenin, various biotin-binding labeling enzyme proteins are reacted, and detection can be performed using the enzyme activity of such labeling enzyme proteins as indices. Various fluorescent substances to be utilized upon fluorescence labeling enable highly sensitive detection by utilizing an optical detection means for observing fluorescence intensity derived from such fluorescent substances. In addition, the aforementioned detection method using the enzyme activity of labeling enzyme protein as an index can also utilize an optical detection means when the enzyme activity utilizes various chromogenic reactions, and enables detection with high sensitivity. The fluorescence intensity value can be read using a focal, non-confocal laser scanner or CCD scanner as the optical detection means.

When an amplification product is hybridized with a DNA microarray, a double stranded DNA product may be subjected to a hybridization reaction with a DNA microarray, or a step of isolating a single strand DNA from an amplified double stranded DNA product before hybridization reaction may be added. From the aspect of detection sensitivity, a step of isolating a single strand DNA is preferably added.

The method of isolating a single strand DNA from a double strand DNA is not particularly limited and, for example, the method disclosed in JP-A-2006-230342 can be mentioned. To be specific, a single strand DNA can be isolated by the following procedure. The 5'-end of a primer for synthesizing a tag chain on the non-detection side is labeled with biotin. After amplification, biotin is bonded to streptavidin-immobilized magnetic beads to form an amplified DNA product-magnetic bead complex. The complex is reacted with an alkali solution such as aqueous NaOH solution and the like, whereby the double strand of the amplified DNA product is dissociated to single strands. Thereafter, the magnetic beads are adsorbed to a magnet, whereby only a single strand DNA elongated by primer not labeled with biotin can be selectively isolated. The outline of the steps for isolation of antisense strand DNA using magnetic beads is shown in FIG. 1. In the steps described in FIG. 1, when a reverse primer with a biotin-modified 5' terminal is used instead of the forward primer with a biotin-modified 5' terminal, isolation of sense strand DNA using magnetic beads can also be performed in the same manner.

Since HPV genetic screening is a test using a clinical sample, experimental accuracy control is extremely important. Hence, setting of a gene to be the internal standard (internal standard gene) is desirable. The internal standard gene in the present specification is a gene to be subjected to multiplex PCR together with a DNA derived from a sample, hybridized with a probe that recognizes an amplification product and detected for detection of a false negative reaction. For this object, a house keeping gene is often utilized, which is expressed in a comparatively high amount in a cell and shows less variation thereof. Specific examples include G3PDH, β-actin and the like.

The kit of the present invention adopts G3PDH as an internal standard, and optionally contains a combination of a primer set (primer set 24) and a probe (probe 24) for G3PDH (see the above-mentioned Table 1 and Table 3). The combination of the primer set and the probe is designed to amplify or hybridize simultaneously with and at the same efficiency as amplification reactions or hybridization reactions of various types of HPV genes.

In one embodiment, the kit of the present invention contains, from among the aforementioned 24 kinds of combinations of primer set and probe, a combination of primer set 3 and probe 3, a combination of primer set 4 and probe 4, and optionally a combination of primer set 24 and probe 24. In this case, the kit can detect HPV16 and HPV18. These HPV subtypes have a particularly high risk of the onset of cervical cancer.

In another embodiment, the kit of the present invention contains, from among the aforementioned 24 kinds of combinations of primer set and probe, a combination of primer set 3 and probe 3, a combination of primer set 4 and probe 4, a combination of primer set 5 and probe 5, a combination of primer set 6 and probe 6, a combination of primer set 7 and probe 7, a combination of primer set 9 and probe 9, a combination of primer set 10 and probe 10, a combination of primer set 13 and probe 13, a combination of primer set 14 and probe 14, a combination of primer set 15 and probe 15, a combination of primer set 18 and probe 18, a combination of primer set 19 and probe 19, a combination of primer set 20 and probe 20, a combination of primer set 23 and probe 23, and optionally a combination of primer set 24 and probe 24. In this case, the kit can detect HPV16, HPV18, HPV30, HPV31, HPV33, HPV35, HPV39, HPV45, HPV51, HPV52, HPV56, HPV58, HPV59 and HPV68. These HPV subtypes are classified to have a high risk of the onset of cervical cancer.

In a further embodiment, the kit of the present invention contains all the aforementioned 23 kinds of combinations of primer set and probe for the detection of HPV, and optionally a combination of primer set 24 and probe 24.

The kit of the present invention can contain, besides each of the aforementioned combinations of primer set and probe, a combination of all the following reagents or an optional combination thereof, and other reagents: buffer, heat-resistant DNA polymerase, positive control HPV DNA, non HPV DNA, internal standard G3PDH DNA, dNTP, fluorochrome labeled base (e.g., Cy3-dUTP), and streptavidin-immobilized magnetic beads.

As another aspect of the present invention, a method of type-specifically detecting the presence or absence of HPV in a sample using the aforementioned kit of the present invention is provided. The method includes a step of performing PCR using DNA extracted from a sample as a template and the aforementioned primer set, and a step of detecting an amplified DNA product.

In another embodiment, the method includes a step of performing PCR using DNA extracted from a sample as a template and the aforementioned primer set, a step of isolating an amplified DNA product as a single strand, and a step of detection by hybridizing the single strand DNA with the aforementioned probe. While the actual procedures of each step are not particularly limited, the method described for explanation of the kit is preferably used as appropriate.

While the present invention is explained in more detail in the following by referring to Examples, the present invention is not at all limited to the following Examples and the like.

EXAMPLES

Unless otherwise specified, respective reagents (buffer, enzyme, solution, compound etc.) to be used in the Examples are those generally used in the art, and are commercially available or can be prepared as reported earlier.

Example 1

Design of Primer and Confirmation of Specificity

The gene sequences of HPV and G3PDH (glyceraldehydes triphosphoric acid dehydrogenase) to be used as internal standard were obtained from public database. The GenBank accession numbers of the 24 kinds of gene sequences used in the present invention are shown in Table 2.

A primer set satisfying the following criteria was designed based on the sequence of each gene: The melting temperature (Tm) is within the range of 60-70° C. (when the Nearest Neighbor method is used. $Na^+$ Conc.: 50 mM); the length of amplification product is within the range of 100-500 bp; the GC content is within the range of 50-60%; it does not contain a sequence having high homology with other kinds of HPV; it does not form a secondary structure in a molecule; and primers do not hybridize with each other. In this way, primer sets specific to each of HPV and G3PDH were designed.

Oligonucleotide DNA was synthesized by a DNA synthesizer based on the sequences of the primer set shown in Table 1.

DNAs encoding HPV6, HPV11, HPV16, HPV18, HPV30, HPV31, HPV33, HPV34, HPV35, HPV39, HPV40, HPV42, HPV45, HPV51, HPV52, HPV53, HPV54, HPV56, HPV58, HPV59, HPV61, HPV66 or HPV68 were each introduced into plasmid pUC18 to give plasmids for 23 kinds of templates.

Then, each DNA of 23 kinds of the plasmids for HPV templates and the genome derived from Jurkat cell (human leukemia T lymphoma) were respectively subjected to PCR reaction using each primer set produced as mentioned above. The composition of the reaction solution is as follows:

TABLE 4

| | |
|---|---|
| 10 × PCR buffer | 2 μL |
| 2.5 mM dNTP | 0.4 μL |
| primer F (4 μM) | 0.5 μL |
| primer R (4 μM) | 0.5 μL |
| DNA Taq polymerase | 0.16 μL |
| DDW (double distilled water) | 15.44 μL |
| template (1 × 10$^6$ copies) | 1 μL |
| Total | 20 μL |

The reaction conditions of PCR employed were as follows: 30 cycles of 95° C. for 4 min, then 95° C. for 30 sec, 60° C. for 30 sec and 72° C. for 1 min, and then 72° C. for 7 min, followed by preservation at 4° C. The obtained amplified DNA product was separated by agarose gel electrophoresis. An amplification product having an anticipated length was obtained for every primer set, and the absence of contaminating amplified product caused by non-specific hybridization was confirmed.

Then, 23 kinds of the plasmids for HPV templates and the genome extracted from Jurkat cell were respectively subjected to PCR reaction using a mixture of 24 kinds of primer sets. The primer sets were mixed in two patterns of concentrations such that the amplification efficiency of each primer set was almost of the same level. The composition of the reaction solution was as follows.

TABLE 5

| | |
|---|---|
| 10 × PCR buffer | 2 μL |
| 2.5 mM dNTP | 0.4 μL |
| primer mixture | 1 μL |
| (final concentration: 0.05 μM or 0.1 μM) | |
| DNA Taq polymerase | 0.16 μL |
| DDW | 15.44 μL |
| template (1 × 10$^6$ copies) | 1 μL |
| Total | 20 μL |

Figure 2:
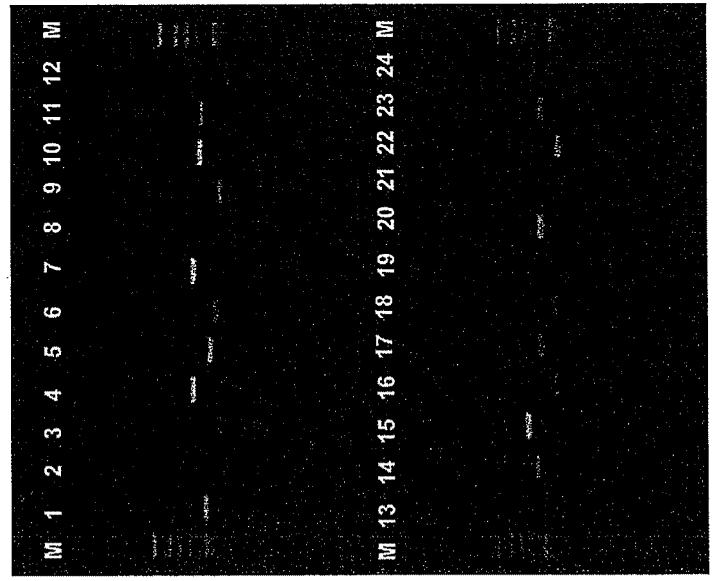
FIG. 2 shows the results of agarose gel electrophoresis of amplified DNA product.

The reaction conditions of PCR employed were as follows: 30 cycles of 95° C. for 4 min, then 95° C. for 30 sec, 60° C. for 30 sec and 72° C. for 1 min, and then 72° C. for 7 min, followed by preservation at 4° C. The obtained amplified DNA product was separated by agarose gel electrophoresis. The results are shown in FIG. 2. An amplification product having an anticipated length was obtained for every template, and therefore, the absence of contaminating amplified product caused by non-specific hybridization was confirmed even when the primers were mixed.

Example 2

Design of Probe

A probe (sense strand DNA) satisfying the following criteria was designed within each PCR amplification region of the 23 kinds of HPV and G3PDH: The melting temperature (Tm) is within the range of 72-78° C. (when the GC % method is used. $Na^+$ Conc.: 50 mM); the length of probe is within the range of 69-71 bp; the GC content is within the range of 45-55%; it does not contain a sequence having high homology with other types of HPV; and it does not form a secondary structure in a molecule. In this way, probes specific to each of HPV and G3PDH were designed (Table 3).

Oligonucleotide DNA was synthesized by a DNA synthesizer based on the sequence of the probe shown in Table 3.

Example 3

Preparation of DNA Microarray

Figure 3:
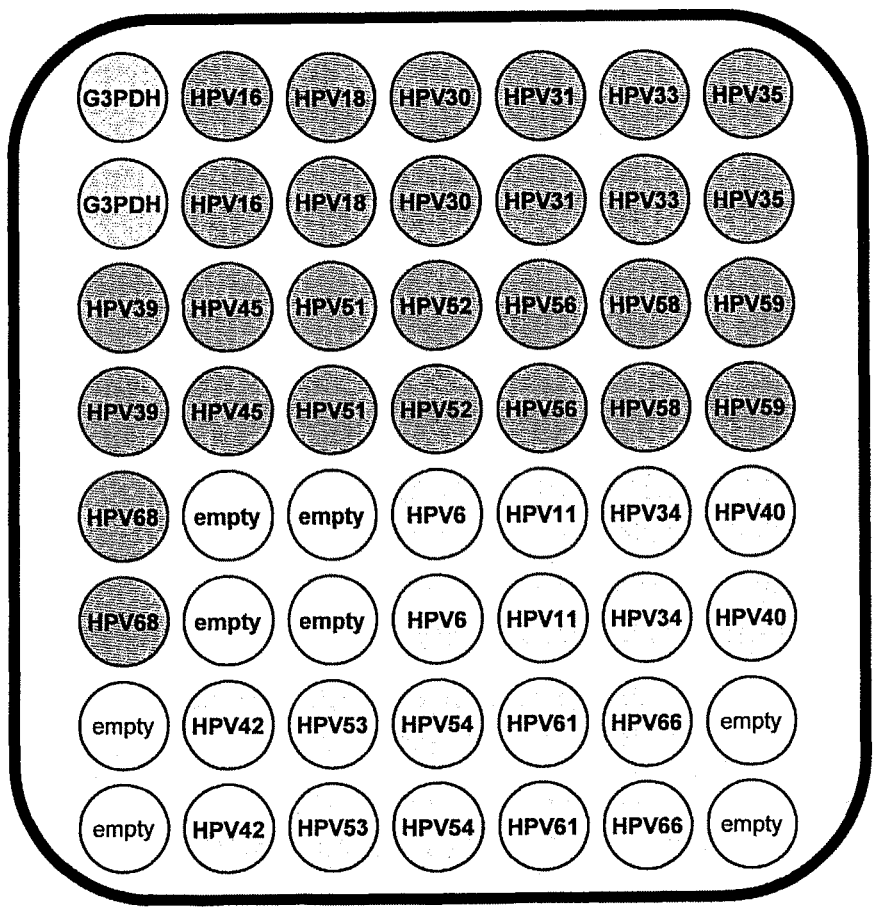
FIG. 3 shows the spot configuration on a prepared DNA microarray.

Each of the 24 kinds of probes synthesized in Example 2 was mixed in the composition shown in Table 6, spotted on a glass substrate coated with poly-L-lysine with a commercially available contact or non-contact type spotter (SpotArray or Piezorray: PerkinElmer) in the arrangement shown in FIG. 3 (2 spots for each probe) to give a DNA microarray for detection.

TABLE 6

| | |
|---|---|
| probe (100 μM) | 5 μL |
| 20 × SSC | 3.75 μL |
| DDW | 16.25 μL |
| Total | 25 μL |

Example 4

Amplification and Detection of HPV (1) Amplification and Labeling of HPV and G3PDH 23 kinds of the plasmids for HPV templates and the genome extracted from Jurkat cell were respectively subjected to PCR reaction at the composition of the reaction mixture shown in Table 7 and using a mixture of 24 kinds of primer sets (primer mixture). The 24 kinds of primer sets were mixed in two patterns of concentrations such that the amplification efficiency of each primer set was almost of the same level. For detection of the presence or absence of HPV infection as fluorescence intensity on the DNA microarray, a fluorochrome labeled base (Cy3-dUTP: GE Healthcare Bio-Sciences Corp.) was simultaneously added to the PCR reaction solution.

TABLE 7

| | |
|---|---|
| 10 × PCR buffer | 2 µL |
| dCTP, dGTP, dATP (each 2.5 mM) | 0.4 µL |
| dTTP (1 mM) | 0.8 µL |
| Cy3-dUTP (1 mM) | 0.2 µL |
| primer mixture | 1 µL |
| (final concentration: 0.05 µM or 0.1 µM) | |
| DNA Taq polymerase | 0.16 µL |
| DDW | 14.44 µL |
| template (1 × $10^4$ copies) | 1 µL |
| Total | 20 µL |

The reaction conditions of PCR employed were as follows: 30 cycles of 95° C. for 4 min, then 95° C. for 30 sec, 60° C. for 30 sec and 72° C. for 1 min, and then 72° C. for 7 min, followed by preservation at 4° C.

From the above, a Cy3-labeled amplified DNA product was obtained.

After the PCR reaction, excess enzyme, fluorochrome labeled base and primer not used for the reaction were removed using a commercially available PCR purification column to purify the Cy3-labeled amplified DNA product.

(2) Detection of HPV Using DNA Microarray

The purified Cy3-labeled amplified DNA product was blended with the hybridization solution described in Table 8, and denatured by heating at 95° C. for 2 min, and the mixture was left standing on ice for 3 min, and 8 µL thereof was used for hybridization with DNA microarray.

TABLE 8

| | |
|---|---|
| Cy3-labeled amplified DNA product | 3.1 µL |
| 20 × SSC | 2.5 µL |
| 50 × Denhardt's solution | 0.8 µL |
| 4% Tween solution | 0.5 µL |
| DDW | 3.1 µL |
| Total | 10 µL |

The hybridization reaction was performed according to the method described in JP-B-3860174 in a thermostatic tank at 65° C. for 1 hr.

After the hybridization reaction, the DNA microarray was washed with 2×SSC-0.1% SDS solution and 0.2×SSC-0.1% SDS solution each for 5 min, rinsed with 0.2×SSC and 0.05× SSC, and dried with a nitrogen gas air gun or slide centrifuge.

This was scanned with a commercially available microarray scanner (GenePix4000B: Axon Instruments). The detection was evaluated from the fluorescence intensity value of the spot at a wavelength of 532 nm and the background value of the periphery of the spot.

A fluorescence spot caused by non-specific hybridization was not detected for any template, and it was confirmed that a fluorescence spot can be detected HPV type-specifically.

Example 5

Detection of HPV Additionally Including Isolation Step of Single Strand DNA Using Magnetic Beads (See FIG. 1)

Of the primer sets designed in Example 1, only primer Fs were newly produced by adding biotin to the 5' end. An order for actual synthesis was placed to a DNA synthesis contractor maker, and the primers were chemically synthesized using a general DNA synthesizer. The amplification and labeling steps of HPV and G3PDH as described in Example 4(1) were performed in the same manner using the primers to give a Cy3-labeled amplified DNA product.

Then, a solution of the Cy3-labeled amplified DNA product was reacted with streptavidin-immobilized magnetic beads (Dynabeads MyOne Streptavidin C1, Invitrogen) for 15 min in a 1.5 mL tube to form an amplified DNA product-magnetic bead complex. The composition of the reaction solution is as follows:

TABLE 9

| | |
|---|---|
| Cy3-labeled amplified DNA product | 10 µL |
| *2 × B&W buffer | 10 µL |
| magnetic beads | 3.5-6 × $10^7$ beads |
| Total | 20 µL |

*composition of 2×B&W buffer: 10 mM Tris-HCl pH 7.5, 1 mM EDTA, 2.0 M NaCl

Thereafter, the reaction solution was completely removed while allowing adsorption of the complex to the magnet. Then, the magnet was removed, a 0.1N NaOH (alkali) solution (10 µL) was added to the complex, and the mixture was reacted for 10 min to dissociate the double strand of the amplified DNA product to a single strand. Thereafter, only the sense strand (single strand) DNA elongated by primer F in the PCR reaction in Table 1 was adsorbed again to the magnet, and the alkali solution was harvested, whereby only the antisense strand DNA elongated by primer R in the PCR reaction was selectively isolated. The isolated antisense strand (single strand) DNA was neutralized with 3M sodium acetic acid (1 µL) and left standing on ice for 5 min.

Then, the isolated antisense strand (single strand) DNA was used for the hybridization reaction with DNA microarray described in Example 4(2). The reaction was performed in the same manner as in Example 4(2) except that the Cy3-labeled amplified DNA product in the reaction composition described in Table 8 was replaced by the antisense strand (single strand) DNA.

Figure 4:
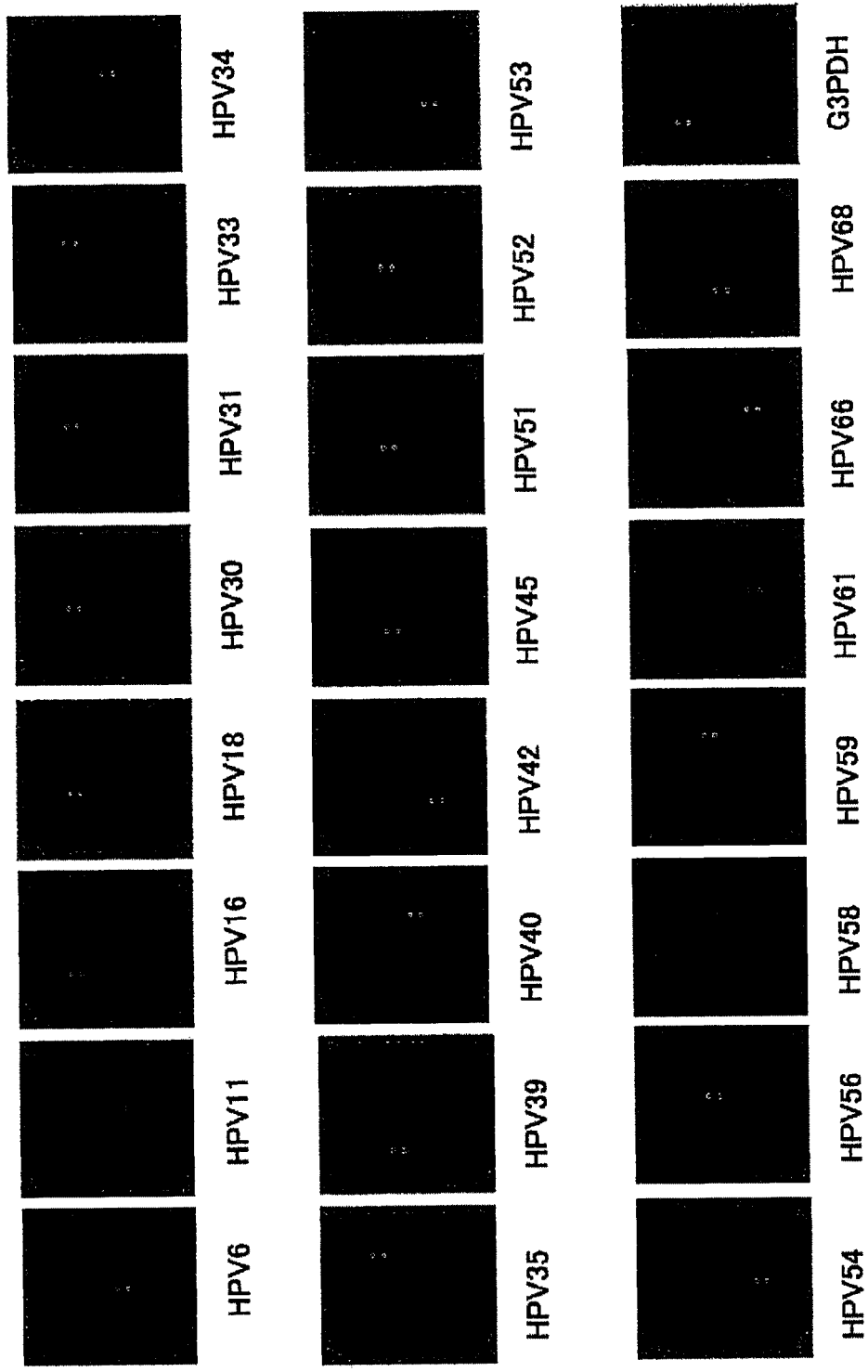
FIG. 4 shows scan images of the detection of the hybridization results of isolated labeled single strand DNA and DNA microarray.
Figure 5:
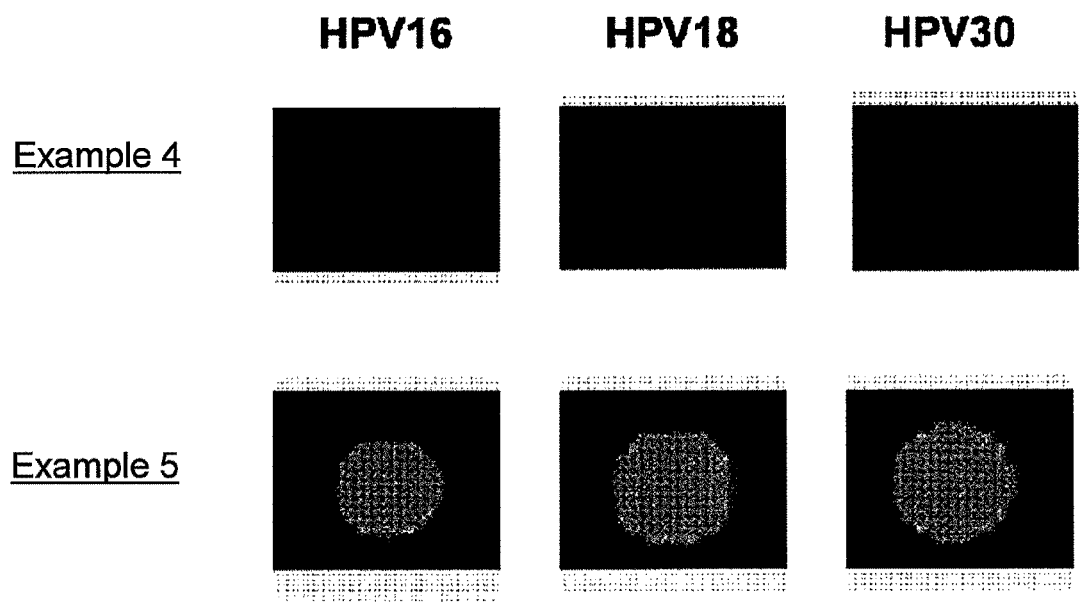
FIG. 5 shows difference in the HPV detection sensitivity between performing and not performing isolation step of single strand DNA using magnetic beads.

The scan images are shown in FIG. 4. A fluorescence spot caused by non-specific hybridization was not detected for any template, and it was confirmed that a fluorescence spot can be detected HPV type-specifically. Furthermore, it could be confirmed that the detection with higher sensitively is possible for any template as compared to Example 4, which results from the addition of the isolation step of single strand DNA using magnetic beads (FIG. 5).

The above-mentioned results show that HPV can be detected with high specificity and high sensitivity by utilizing the primer set and probe of the present invention, and the detection method of HPV of the present invention.

Industrial Applicability

The present invention provides primer set and probe which can rapidly and conveniently detect multiple types of HPV with high specificity and high sensitivity. The present invention also provides a method capable of rapidly and conveniently detecting multiple types of HPV with high specificity and high sensitivity by utilizing the aforementioned primer sets and probes.

This application is based on a patent application No. 2007-203677 filed in Japan (filing date: Aug. 3, 2007), the contents of which are incorporated in full herein by this reference.

SEQUENCE LISTING FREE TEXT

SEQ ID NO: 1: forward PCR primer for HPV6 gene amplification
SEQ ID NO: 2: reverse PCR primer for HPV6 gene amplification
SEQ ID NO: 3: forward PCR primer for HPV11 gene amplification
SEQ ID NO: 4: reverse PCR primer for HPV11 gene amplification
SEQ ID NO: 5: forward PCR primer for HPV16 gene amplification
SEQ ID NO: 6: reverse PCR primer for HPV16 gene amplification
SEQ ID NO: 7: forward PCR primer for HPV18 gene amplification
SEQ ID NO: 8: reverse PCR primer for HPV18 gene amplification
SEQ ID NO: 9: forward PCR primer for HPV30 gene amplification
SEQ ID NO: 10: reverse PCR primer for HPV30 gene amplification
SEQ ID NO: 11: forward PCR primer for HPV31 gene amplification
SEQ ID NO: 12: reverse PCR primer for HPV31 gene amplification
SEQ ID NO: 13: forward PCR primer for HPV33 gene amplification
SEQ ID NO: 14: reverse PCR primer for HPV33 gene amplification
SEQ ID NO: 15: forward PCR primer for HPV34 gene amplification
SEQ ID NO: 16: reverse PCR primer for HPV34 gene amplification
SEQ ID NO: 17: forward PCR primer for HPV35 gene amplification
SEQ ID NO: 18: reverse PCR primer for HPV35 gene amplification
SEQ ID NO: 19: forward PCR primer for HPV39 gene amplification
SEQ ID NO: 20: reverse PCR primer for HPV39 gene amplification
SEQ ID NO: 21: forward PCR primer for HPV40 gene amplification
SEQ ID NO: 22: reverse PCR primer for HPV40 gene amplification
SEQ ID NO: 23: forward PCR primer for HPV42 gene amplification
SEQ ID NO: 24: reverse PCR primer for HPV42 gene amplification
SEQ ID NO: 25: forward PCR primer for HPV45 gene amplification
SEQ ID NO: 26: reverse PCR primer for HPV45 gene amplification
SEQ ID NO: 27: forward PCR primer for HPV51 gene amplification
SEQ ID NO: 28: reverse PCR primer for HPV51 gene amplification
SEQ ID NO: 29: forward PCR primer for HPV52 gene amplification
SEQ ID NO: 30: reverse PCR primer for HPV52 gene amplification
SEQ ID NO: 31: forward PCR primer for HPV53 gene amplification
SEQ ID NO: 32: reverse PCR primer for HPV53 gene amplification
SEQ ID NO: 33: forward PCR primer for HPV54 gene amplification
SEQ ID NO: 34: reverse PCR primer for HPV54 gene amplification
SEQ ID NO: 35: forward PCR primer for HPV56 gene amplification
SEQ ID NO: 36: reverse PCR primer for HPV56 gene amplification
SEQ ID NO: 37: forward PCR primer for HPV58 gene amplification
SEQ ID NO: 38: reverse PCR primer for HPV58 gene amplification
SEQ ID NO: 39: forward PCR primer for HPV59 gene amplification
SEQ ID NO: 40: reverse PCR primer for HPV59 gene amplification
SEQ ID NO: 41: forward PCR primer for HPV61 gene amplification
SEQ ID NO: 42: reverse PCR primer for HPV61 gene amplification
SEQ ID NO: 43: forward PCR primer for HPV66 gene amplification
SEQ ID NO: 44: reverse PCR primer for HPV66 gene amplification
SEQ ID NO: 45: forward PCR primer for HPV68 gene amplification
SEQ ID NO: 46: reverse PCR primer for HPV68 gene amplification
SEQ ID NO: 47: forward PCR primer for G3PDH gene amplification
SEQ ID NO: 48: reverse PCR primer for G3PDH gene amplification
SEQ ID NO: 49: probe for HPV6 gene detection
SEQ ID NO: 50: probe for HPV11 gene detection
SEQ ID NO: 51: probe for HPV16 gene detection
SEQ ID NO: 52: probe for HPV18 gene detection
SEQ ID NO: 53: probe for HPV30 gene detection
SEQ ID NO: 54: probe for HPV31 gene detection
SEQ ID NO: 55: probe for HPV33 gene detection
SEQ ID NO: 56: probe for HPV34 gene detection
SEQ ID NO: 57: probe for HPV35 gene detection
SEQ ID NO: 58: probe for HPV39 gene detection
SEQ ID NO: 59: probe for HPV40 gene detection
SEQ ID NO: 60: probe for HPV42 gene detection
SEQ ID NO: 61: probe for HPV45 gene detection
SEQ ID NO: 62: probe for HPV51 gene detection
SEQ ID NO: 63: probe for HPV52 gene detection
SEQ ID NO: 64: probe for HPV53 gene detection
SEQ ID NO: 65: probe for HPV54 gene detection
SEQ ID NO: 66: probe for HPV56 gene detection
SEQ ID NO: 67: probe for HPV58 gene detection
SEQ ID NO: 68: probe for HPV59 gene detection
SEQ ID NO: 69: probe for HPV61 gene detection
SEQ ID NO: 70: probe for HPV66 gene detection
SEQ ID NO: 71: probe for HPV68 gene detection
SEQ ID NO: 72: probe for G3PDH gene detection

The invention claimed is:

1. A kit for the detection of two or more types of human papillomavirus (HPV), comprising two or more combinations selected from the group consisting of (1) a combination of primer set 1 consisting of a primer consisting of the base sequence of SEQ ID NO: 1 and a primer consisting of the base sequence of SEQ ID NO: 2, and a probe consisting of a base sequence with not less than 95% identity with the base sequence of SEQ ID NO: 49, or a probe consisting of a base sequence with not less than 95% identity with the base sequence complementary to the base sequence of SEQ ID NO: 49 (probe 1), (2) a combination of primer set 2 consisting of a primer consisting of the base sequence of SEQ ID NO: 3 and a primer consisting of the base sequence of SEQ ID NO: 4, and a probe consisting of a base sequence with not less than 95% identity with the base sequence of SEQ ID NO: 50, or a probe consisting of a base sequence with not less than 95% identity with the base sequence complementary to the base sequence of SEQ ID NO: 50 (probe 2), (3) a combination of primer set 3 consisting of a primer consisting of the base sequence of SEQ ID NO: 5 and a primer consisting of base sequence of SEQ ID NO: 6, and a probe consisting of a base sequence with not less than 95% identity with the base sequence of SEQ ID NO: 51, or a probe consisting of a base sequence with not less than 95% identity with the base sequence complementary to the base sequence of SEQ ID NO: 51 (probe 3), (4) a combination of primer set 4 consisting of a primer consisting of the base sequence of SEQ ID NO: 7 and a primer consisting of the base sequence shown by SEQ ID NO: 8, and a probe consisting of a base sequence with not less than 95% identity with the base sequence of SEQ ID NO: 52, or a probe consisting of a base sequence with not less than 95% identity with the base sequence complementary to the base sequence of SEQ ID NO: 52 (probe 4), (5) a combination of primer set 5 consisting of a primer consisting of the base sequence of SEQ ID NO: 9 and a primer consisting of the base sequence of SEQ ID NO: 10, and a probe consisting of a base sequence with not less than 95% identity with the base sequence of SEQ ID NO: 53, or a probe consisting of a base sequence with not less than 95% identity with the base sequence complementary to the base sequence of SEQ ID NO: 53 (probe 5), (6) a combination of primer set 6 consisting of a primer consisting of the base sequence of SEQ ID NO: 11 and a primer consisting of the base sequence of SEQ ID NO: 12, and a probe consisting of a base sequence with not less than 95% identity with the base sequence of SEQ ID NO: 54, or a probe consisting of a base sequence with not less than 95% identity with the base sequence complementary to the base sequence of SEQ ID NO: 54 (probe 6), (7) a combination of primer set 7 consisting of a primer consisting of the base sequence of SEQ ID NO: 13 and a primer consisting of the base sequence of SEQ ID NO: 14, and a probe consisting of a base sequence with not less than 95% identity with the base sequence of SEQ ID NO: 55, or a probe consisting of a base sequence with not less than 95% identity with the base sequence complementary to the base sequence of SEQ ID NO: 55 (probe 7), (8) a combination of primer set 8 consisting of a primer consisting of the base sequence of SEQ ID NO: 15 and a primer consisting of the base sequence of SEQ ID NO: 16, and a probe consisting of a base sequence with not less than 95% identity with the base sequence of SEQ ID NO: 56, or a probe consisting of a base sequence with not less than 95% identity with the base sequence complementary to the base sequence of SEQ ID NO: 56 (probe 8), (9) a combination of primer set 9 consisting of a primer consisting of the base sequence of SEQ ID NO: 17 and a primer consisting of the base sequence of SEQ ID NO: 18, and a probe consisting of a base sequence with not less than 95% identity with the base sequence of SEQ ID NO: 57, or a probe consisting of a base sequence with not less than 95% identity with the base sequence complementary to the base sequence of SEQ ID NO: 57 (probe 9),

(10) a combination of primer set 10 consisting of a primer consisting of the base sequence of SEQ ID NO: 19 and a primer consisting of the base sequence of SEQ ID NO: 20, and a probe consisting of a base sequence with not less than 95% identity with the base sequence of SEQ ID NO: 58, or a probe consisting of a base sequence with not less than 95% identity with the base sequence complementary to the base sequence of SEQ ID NO: 58 (probe 10),

(11) a combination of primer set 11 consisting of a primer consisting of the base sequence of SEQ ID NO: 21 and a primer consisting of the base sequence of SEQ ID NO: 22, and a probe consisting of a base sequence with not less than 95% identity with the base sequence of SEQ ID NO: 59, or a probe consisting of a base sequence with not less than 95% identity with the base sequence complementary to the base sequence shown by SEQ ID NO: 59 (probe 11),

(12) a combination of primer set 12 consisting of a primer consisting of the base sequence of SEQ ID NO: 23 and a primer consisting of the base sequence of SEQ ID NO: 24, and a probe consisting of a base sequence with not less than 95% identity with the base sequence of SEQ ID NO: 60, or a probe consisting of a base sequence with not less than 95% identity with the base sequence complementary to the base sequence of SEQ ID NO: 60 (probe 12),

(13) a combination of primer set 13 consisting of a primer consisting of the base sequence of SEQ ID NO: 25 and a primer consisting of the base sequence of SEQ ID NO: 26, and a probe consisting of a base sequence with not less than 95% identity with the base sequence of SEQ ID NO: 61, or a probe consisting of a base sequence with not less than 95% identity with the base sequence complementary to the base sequence of SEQ ID NO: 61 (probe 13),

(14) a combination of primer set 14 consisting of a primer consisting of the base sequence of SEQ ID NO: 27 and a primer consisting of the base sequence of SEQ ID NO: 28, and a probe consisting of a base sequence with not less than 95% identity with the base sequence of SEQ ID NO: 62, or a probe consisting of a base sequence with not less than 95% identity with the base sequence complementary to the base sequence of SEQ ID NO: 62 (probe 14),

(15) a combination of primer set 15 consisting of a primer consisting of the base sequence of SEQ ID NO: 29 and a primer consisting of the base sequence of SEQ ID NO: 30, and a probe consisting of a base sequence with not less than 95% identity with the base sequence of SEQ ID NO: 63, or a probe consisting of a base sequence with not less than 95% identity with the base sequence complementary to the base sequence shown by SEQ ID NO: 63 (probe 15),

(16) a combination of primer set 16 consisting of a primer consisting of the base sequence of SEQ ID NO: 31 and a primer consisting of the base sequence of SEQ ID NO: 32, and a probe consisting of a base sequence with not less than 95% identity with the base sequence of SEQ ID NO: 64, or a probe consisting of a base sequence with not less than 95% identity with the base sequence complementary to the base sequence of SEQ ID NO: 64 (probe 16),

(17) a combination of primer set 17 consisting of a primer consisting of the base sequence of SEQ ID NO: 33 and a primer consisting of the base sequence of SEQ ID NO: 34, and a probe consisting of a base sequence with not less than 95% identity with the base sequence of SEQ ID NO: 65, or a probe consisting of a base sequence with not less than 95% identity with the base sequence complementary to the base sequence of SEQ ID NO: 65 (probe 17),

(18) a combination of primer set 18 consisting of a primer consisting of the base sequence of SEQ ID NO: 35 and a primer consisting of the base sequence of SEQ ID NO: 36, and a probe consisting of a base sequence with not less than 95% identity with the base sequence of SEQ ID NO: 66, or a probe consisting of a base sequence with not less than 95% identity with the base sequence complementary to the base sequence of SEQ ID NO: 66 (probe 18),

(19) a combination of primer set 19 consisting of a primer consisting of the base sequence of SEQ ID NO: 37 and a primer consisting of the base sequence of SEQ ID NO: 38, and a probe consisting of a base sequence with not less than 95% identity with the base sequence of SEQ ID NO: 67, or a probe consisting of a base sequence with not less than 95% identity with the base sequence complementary to the base sequence of SEQ ID NO: 67 (probe 19),

(20) a combination of primer set 20 consisting of a primer consisting of the base sequence of SEQ ID NO: 39 and a primer consisting of the base sequence of SEQ ID NO: 40, and a probe consisting of a base sequence with not less than 95% identity with the base sequence of SEQ ID NO: 68, or a probe consisting of a base sequence with not less than 95% identity with the base sequence complementary to the base sequence of SEQ ID NO: 68 (probe 20),

(21) a combination of primer set 21 consisting of a primer consisting of the base sequence of SEQ ID NO: 41 and a primer consisting of the base sequence of SEQ ID NO: 42, and a probe consisting of a base sequence with not less than 95% identity with the base sequence of SEQ ID NO: 69, or a probe consisting of a base sequence with not less than 95% identity with the base sequence complementary to the base sequence of SEQ ID NO: 69 (probe 21),

(22) a combination of primer set 22 consisting of a primer consisting of the base sequence of SEQ ID NO: 43 and a primer consisting of the base sequence of SEQ ID NO: 44, and a probe consisting of a base sequence with not less than 95% identity with the base sequence of SEQ ID NO: 70, or a probe consisting of a base sequence with not less than 95% identity with the base sequence complementary to the base sequence of SEQ ID NO: 70 (probe 22), and

(23) a combination of primer set 23 consisting of a primer consisting of the base sequence of SEQ ID NO: 45 and a primer consisting of the base sequence of SEQ ID NO: 46, and a probe consisting of a base sequence with not less than 95% identity with the base sequence of SEQ ID NO: 71, or a probe consisting of a base sequence with not less than 95% identity with the base sequence complementary to the base sequence of SEQ ID NO: 71 (probe 23).

2. The kit according to claim 1, comprising a combination of primer set 3 and probe 3, and a combination of primer set 4 and probe 4.

3. The kit according to claim 1, comprising a combination of primer set 3 and probe 3, a combination of primer set 4 and probe 4, a combination of primer set 5 and probe 5, a combination of primer set 6 and probe 6, a combination of primer set 7 and probe 7, a combination of primer set 9 and probe 9, a combination of primer set 10 and probe 10, a combination of primer set 13 and probe 13, a combination of primer set 14 and probe 14, a combination of primer set 15 and probe 15, a combination of primer set 18 and probe 18, a combination of primer set 19 and probe 19, a combination of primer set 20 and probe 20, and a combination of primer set 23 and probe 23.

4. The kit according to claim 1, comprising a combination of primer set 1 and probe 1, a combination of primer set 2 and probe 2, a combination of primer set 3 and probe 3, a combination of primer set 4 and probe 4, a combination of primer set 5 and probe 5, a combination of primer set 6 and probe 6, a combination of primer set 7 and probe 7, a combination of primer set 8 and probe 8, a combination of primer set 9 and probe 9, a combination of primer set 10 and probe 10, a combination of primer set 11 and probe 11, a combination of primer set 12 and probe 12, a combination of primer set 13 and probe 13, a combination of primer set 14 and probe 14, a combination of primer set 15 and probe 15, a combination of primer set 16 and probe 16, a combination of primer set 17 and probe 17, a combination of primer set 18 and probe 18, a combination of primer set 19 and probe 19, a combination of primer set 20 and probe 20, a combination of primer set 21 and probe 21, a combination of primer set 22 and probe 22, and a combination of primer set 23 and probe 23.

5. A method of type-specifically detecting the presence or absence of HPV in a sample by using the kit according to claim 1, comprising a step of performing PCR using the aforementioned primer sets and DNA extracted from the sample as a template, and a step of detecting an amplified DNA product by using the aforementioned probes.

6. A method of type-specifically detecting the presence or absence of HPV in a sample by using the kit according to claim 1, comprising a step of performing PCR using the aforementioned primer sets and DNA extracted from the sample as a template, a step of processing an amplified DNA product to have a single strand, and a step of hybridizing the single strand DNA with the aforementioned probe, followed by detection.

7. A method of type-specifically detecting the presence or absence of HPV in a sample by using the kit according to claim 2, comprising a step of performing PCR using the aforementioned primer sets and DNA extracted from the sample as a template, and a step of detecting an amplified DNA product by using the aforementioned probes.

8. A method of type-specifically detecting the presence or absence of HPV in a sample by using the kit according to claim 3, comprising a step of performing PCR using the aforementioned primer sets and DNA extracted from the sample as a template, and a step of detecting an amplified DNA product by using the aforementioned probes.

9. A method of type-specifically detecting the presence or absence of HPV in a sample by using the kit according to claim 4, comprising a step of performing PCR using the aforementioned primer sets and DNA extracted from the sample as a template, and a step of detecting an amplified DNA product by using the aforementioned probes.

10. A method of type-specifically detecting the presence or absence of HPV in a sample by using the kit according to claim 2, comprising a step of performing PCR using the aforementioned primer sets and DNA extracted from the sample as a template, a step of processing an amplified DNA product to have a single strand, and a step of hybridizing the single strand DNA with the aforementioned probe, followed by detection.

11. A method of type-specifically detecting the presence or absence of HPV in a sample by using the kit according to claim 3, comprising a step of performing PCR using the aforementioned primer sets and DNA extracted from the sample as a template, a step of processing an amplified DNA product to have a single strand, and a step of hybridizing the single strand DNA with the aforementioned probe, followed by detection.

12. A method of type-specifically detecting the presence or absence of HPV in a sample by using the kit according to claim 4, comprising a step of performing PCR using the aforementioned primer sets and DNA extracted from the sample as a template, a step of processing an amplified DNA product to have a single strand, and a step of hybridizing the single strand DNA with the aforementioned probe, followed by detection.

13. The kit according to claim 1, wherein:
probe 1 consists of (i) the base sequence of SEQ ID NO: 49, (ii) the base sequence of SEQ ID NO: 49 in which one nucleotide is substituted, deleted, inserted or added, (iii) the base sequence complementary to the base sequence of SEQ ID NO: 49, or (iv) the base sequence complementary to the base sequence of SEQ ID NO: 49 in which one nucleotide is substituted, deleted, inserted or added;
probe 2 consists of (i) the base sequence of SEQ ID NO: 50, (ii) the base sequence of SEQ ID NO: 50 in which one nucleotide is substituted, deleted, inserted or added, (iii) the base sequence complementary to the base sequence of SEQ ID NO: 50, or (iv) the base sequence complementary to the base sequence of SEQ ID NO: 50 in which one nucleotide is substituted, deleted, inserted or added;
probe 3 consists of (i) the base sequence of SEQ ID NO: 51, (ii) the base sequence of SEQ ID NO: 51 in which one nucleotide is substituted, deleted, inserted or added, (iii) the base sequence complementary to the base sequence of SEQ ID NO: 51, or (iv) the base sequence complementary to the base sequence of SEQ ID NO: 51 in which one nucleotide is substituted, deleted, inserted or added;
probe 4 consists of (i) the base sequence of SEQ ID NO: 52, (ii) the base sequence of SEQ ID NO: 52 in which one nucleotide is substituted, deleted, inserted or added, (iii) the base sequence complementary to the base sequence of SEQ ID NO: 52, or (iv) the base sequence complementary to the base sequence of SEQ ID NO: 52 in which one nucleotide is substituted, deleted, inserted or added;
probe 5 consists of (i) the base sequence of SEQ ID NO: 53, (ii) the base sequence of SEQ ID NO: 53 in which one nucleotide is substituted, deleted, inserted or added, (iii) the base sequence complementary to the base sequence of SEQ ID NO: 53, or (iv) the base sequence complementary to the base sequence of SEQ ID NO: 53 in which one nucleotide is substituted, deleted, inserted or added;

probe 6 consists of (i) the base sequence of SEQ ID NO: 54, (ii) the base sequence of SEQ ID NO: 54 in which one nucleotide is substituted, deleted, inserted or added, (iii) the base sequence complementary to the base sequence of SEQ ID NO: 54, or (iv) the base sequence complementary to the base sequence of SEQ ID NO: 54 in which one nucleotide is substituted, deleted, inserted or added;

probe 7 consists of (i) the base sequence of SEQ ID NO: 55, (ii) the base sequence of SEQ ID NO: 55 in which one nucleotide is substituted, deleted, inserted or added, (iii) the base sequence complementary to the base sequence of SEQ ID NO: 55, or (iv) the base sequence complementary to the base sequence of SEQ ID NO: 55 in which one nucleotide is substituted, deleted, inserted or added;

probe 8 consists of (i) the base sequence of SEQ ID NO: 56, (ii) the base sequence of SEQ ID NO: 56 in which one nucleotide is substituted, deleted, inserted or added, (iii) the base sequence complementary to the base sequence of SEQ ID NO: 56, or (iv) the base sequence complementary to the base sequence of SEQ ID NO: 56 in which one nucleotide is substituted, deleted, inserted or added;

probe 9 consists of (i) the base sequence of SEQ ID NO: 57, (ii) the base sequence of SEQ ID NO: 57 in which one nucleotide is substituted, deleted, inserted or added, (iii) the base sequence complementary to the base sequence of SEQ ID NO: 57, or (iv) the base sequence complementary to the base sequence of SEQ ID NO: 57 in which one nucleotide is substituted, deleted, inserted or added;

probe 10 consists of (i) the base sequence of SEQ ID NO: 58, (ii) the base sequence of SEQ ID NO: 58 in which one nucleotide is substituted, deleted, inserted or added, (iii) the base sequence complementary to the base sequence of SEQ ID NO: 58, or (iv) the base sequence complementary to the base sequence of SEQ ID NO: 58 in which one nucleotide is substituted, deleted, inserted or added;

probe 11 consists of (i) the base sequence of SEQ ID NO: 59, (ii) the base sequence of SEQ ID NO: 59 in which one nucleotide is substituted, deleted, inserted or added, (iii) the base sequence complementary to the base sequence of SEQ ID NO: 59, or (iv) the base sequence complementary to the base sequence of SEQ ID NO: 59 in which one nucleotide is substituted, deleted, inserted or added;

probe 12 consists of (i) the base sequence of SEQ ID NO: 60, (ii) the base sequence of SEQ ID NO: 60 in which one nucleotide is substituted, deleted, inserted or added, (iii) the base sequence complementary to the base sequence of SEQ ID NO: 60, or (iv) the base sequence complementary to the base sequence of SEQ ID NO: 60 in which one nucleotide is substituted, deleted, inserted or added;

probe 13 consists of (i) the base sequence of SEQ ID NO: 61, (ii) the base sequence of SEQ ID NO: 61 in which one nucleotide is substituted, deleted, inserted or added, (iii) the base sequence complementary to the base sequence of SEQ ID NO: 61, or (iv) the base sequence complementary to the base sequence of SEQ ID NO: 61 in which one nucleotide is substituted, deleted, inserted or added;

probe 14 consists of (i) the base sequence of SEQ ID NO: 62, (ii) the base sequence of SEQ ID NO: 62 in which one nucleotide is substituted, deleted, inserted or added, (iii) the base sequence complementary to the base sequence of SEQ ID NO: 62, or (iv) the base sequence complementary to the base sequence of SEQ ID NO: 62 in which one nucleotide is substituted, deleted, inserted or added;

probe 15 consists of (i) the base sequence of SEQ ID NO: 63, (ii) the base sequence of SEQ ID NO: 63 in which one nucleotide is substituted, deleted, inserted or added, (iii) the base sequence complementary to the base sequence of SEQ ID NO: 63, or (iv) the base sequence complementary to the base sequence of SEQ ID NO: 63 in which one nucleotide is substituted, deleted, inserted or added;

probe 16 consists of (i) the base sequence of SEQ ID NO: 64, (ii) the base sequence of SEQ ID NO: 64 in which one nucleotide is substituted, deleted, inserted or added, (iii) the base sequence complementary to the base sequence of SEQ ID NO: 64, or (iv) the base sequence complementary to the base sequence of SEQ ID NO: 64 in which one nucleotide is substituted, deleted, inserted or added;

probe 17 consists of (i) the base sequence of SEQ ID NO: 65, (ii) the base sequence of SEQ ID NO: 65 in which one nucleotide is substituted, deleted, inserted or added, (iii) the base sequence complementary to the base sequence of SEQ ID NO: 65, or (iv) the base sequence complementary to the base sequence of SEQ ID NO: 65 in which one nucleotide is substituted, deleted, inserted or added;

probe 18 consists of (i) the base sequence of SEQ ID NO: 66, (ii) the base sequence of SEQ ID NO: 66 in which one nucleotide is substituted, deleted, inserted or added, (iii) the base sequence complementary to the base sequence of SEQ ID NO: 66, or (iv) the base sequence complementary to the base sequence of SEQ ID NO: 66 in which one nucleotide is substituted, deleted, inserted or added;

probe 19 consists of (i) the base sequence of SEQ ID NO: 67, (ii) the base sequence of SEQ ID NO: 67 in which one nucleotide is substituted, deleted, inserted or added, (iii) the base sequence complementary to the base sequence of SEQ ID NO: 67, or (iv) the base sequence complementary to the base sequence of SEQ ID NO: 67 in which one nucleotide is substituted, deleted, inserted or added;

probe 20 consists of (i) the base sequence of SEQ ID NO: 68, (ii) the base sequence of SEQ ID NO: 68 in which one nucleotide is substituted, deleted, inserted or added, (iii) the base sequence complementary to the base sequence of SEQ ID NO: 68, or (iv) the base sequence complementary to the base sequence of SEQ ID NO: 68 in which one nucleotide is substituted, deleted, inserted or added;

probe 21 consists of (i) the base sequence of SEQ ID NO: 69, (ii) the base sequence of SEQ ID NO: 69 in which one nucleotide is substituted, deleted, inserted or added, (iii) the base sequence complementary to the base sequence of SEQ ID NO: 69, or (iv) the base sequence complementary to the base sequence of SEQ ID NO: 69 in which one nucleotide is substituted, deleted, inserted or added;

probe 22 consists of (i) the base sequence of SEQ ID NO: 70, (ii) the base sequence of SEQ ID NO: 70 in which one nucleotide is substituted, deleted, inserted or added, (iii) the base sequence complementary to the base sequence of SEQ ID NO: 70, or (iv) the base sequence complementary to the base sequence of SEQ ID NO: 70 in which one nucleotide is substituted, deleted, inserted or added; and probe 23 consists of (i) the base sequence of SEQ ID NO: 71, (ii) the base sequence of SEQ ID NO: 71 in which one nucleotide is substituted, deleted, inserted or added, (iii) the base sequence complementary to the base sequence of SEQ ID NO: 71, or (iv) the base sequence complementary to the base sequence of SEQ ID NO: 71 in which one nucleotide is substituted, deleted, inserted or added.

14. The kit according to claim 1, wherein:

probe 1 consists of the base sequence of SEQ ID NO: 49 or the base sequence complementary to the base sequence of SEQ ID NO: 49;

probe 2 consists of the base sequence of SEQ ID NO: 50 or the base sequence complementary to the base sequence of SEQ ID NO: 50;

probe 3 consists of the base sequence of SEQ ID NO: 51 or the base sequence complementary to the base sequence of SEQ ID NO: 51;

probe 4 consists of the base sequence of SEQ ID NO: 52 or the base sequence complementary to the base sequence of SEQ ID NO: 52;

probe 5 consists of the base sequence of SEQ ID NO: 53 or the base sequence complementary to the base sequence of SEQ ID NO: 53;

probe 6 consists of the base sequence of SEQ ID NO: 54 or the base sequence complementary to the base sequence of SEQ ID NO: 54;

probe 7 consists of the base sequence of SEQ ID NO: 55 or the base sequence complementary to the base sequence of SEQ ID NO: 55;

probe 8 consists of the base sequence of SEQ ID NO: 56 or the base sequence complementary to the base sequence of SEQ ID NO: 56;

probe 9 consists of the base sequence of SEQ ID NO: 57 or the base sequence complementary to the base sequence of SEQ ID NO: 57;

probe 10 consists of the base sequence of SEQ ID NO: 58 or the base sequence complementary to the base sequence of SEQ ID NO: 58;

probe 11 consists of the base sequence of SEQ ID NO: 59 or the base sequence complementary to the base sequence of SEQ ID NO: 59;

probe 12 consists of the base sequence of SEQ ID NO: 60 or the base sequence complementary to the base sequence of SEQ ID NO: 60;

probe 13 consists of the base sequence of SEQ ID NO: 61 or the base sequence complementary to the base sequence of SEQ ID NO: 61;

probe 14 consists of the base sequence of SEQ ID NO: 62 or the base sequence complementary to the base sequence of SEQ ID NO: 62;

probe 15 consists of the base sequence of SEQ ID NO: 63 or the base sequence complementary to the base sequence of SEQ ID NO: 63;

probe 16 consists of the base sequence of SEQ ID NO: 64 or the base sequence complementary to the base sequence of SEQ ID NO: 64;

probe 17 consists of the base sequence of SEQ ID NO: 65 or the base sequence complementary to the base sequence of SEQ ID NO: 65;

probe 18 consists of the base sequence of SEQ ID NO: 66 or the base sequence complementary to the base sequence of SEQ ID NO: 66;

probe 19 consists of the base sequence of SEQ ID NO: 67 or the base sequence complementary to the base sequence of SEQ ID NO: 67;

probe 20 consists of the base sequence of SEQ ID NO: 68 or the base sequence complementary to the base sequence of SEQ ID NO: 68;

probe 21 consists of the base sequence of SEQ ID NO: 69 or the base sequence complementary to the base sequence of SEQ ID NO: 69;

probe 22 consists of the base sequence of SEQ ID NO: 70 or the base sequence complementary to the base sequence of SEQ ID NO: 70; and probe 23 consists of the base sequence of SEQ ID NO: 71 or the base sequence complementary to the base sequence of SEQ ID NO: 71.

15. The kit according to claim 1, further comprising a means for isolating a single strand from the amplified DNA product.

16. The kit according to claim 15, wherein the means comprises a magnetic bead.

* * * * *

SEQUENCE LISTING

<160> NUMBER OF SEQ ID NOS: 72

<210> SEQ ID NO 1
<211> LENGTH: 21
<212> TYPE: DNA
<213> ORGANISM: Artificial Sequence
<220> FEATURE:
<223> OTHER INFORMATION: A forward PCR primer for HPV6 gene.

<400> SEQUENCE: 1
tctgctgccc ctaaacgtaa g                                           21

<210> SEQ ID NO 2
<211> LENGTH: 21
<212> TYPE: DNA
<213> ORGANISM: Artificial Sequence
<220> FEATURE:
<223> OTHER INFORMATION: A reverse PCR primer for HPV6 gene.

<400> SEQUENCE: 2
ggtggaaagt gtatgccaag g                                           21

<210> SEQ ID NO 3
<211> LENGTH: 19
<212> TYPE: DNA
<213> ORGANISM: Artificial Sequence
<220> FEATURE:
<223> OTHER INFORMATION: A forward PCR primer for HPV11 gene.

<400> SEQUENCE: 3
cgttttcggt tgcccttac                                              19

<210> SEQ ID NO 4
<211> LENGTH: 19
<212> TYPE: DNA
<213> ORGANISM: Artificial Sequence
<220> FEATURE:
<223> OTHER INFORMATION: A reverse PCR primer for HPV11 gene.

<400> SEQUENCE: 4
acctttggct gcaatccac                                              19

<210> SEQ ID NO 5
<211> LENGTH: 18
<212> TYPE: DNA
<213> ORGANISM: Artificial Sequence
<220> FEATURE:
<223> OTHER INFORMATION: A forward PCR primer for HPV16 gene.

<400> SEQUENCE: 5
cggttgcatg cttttttgg                                              18

<210> SEQ ID NO 6
<211> LENGTH: 20
<212> TYPE: DNA
<213> ORGANISM: Artificial Sequence
<220> FEATURE:
<223> OTHER INFORMATION: A reverse PCR primer for HPV16 gene.

<400> SEQUENCE: 6
cagcggtatg taaggcgttg                                             20

<210> SEQ ID NO 7
<211> LENGTH: 20
<212> TYPE: DNA

```
<213> ORGANISM: Artificial Sequence
<220> FEATURE:
<223> OTHER INFORMATION: A forward PCR primer for HPV18 gene.

<400> SEQUENCE: 7
ctgcaccggc tgaaaataag                                              20

<210> SEQ ID NO 8
<211> LENGTH: 20
<212> TYPE: DNA
<213> ORGANISM: Artificial Sequence
<220> FEATURE:
<223> OTHER INFORMATION: A reverse PCR primer for HPV18 gene.

<400> SEQUENCE: 8
atagcccaac aagcaacacc                                              20

<210> SEQ ID NO 9
<211> LENGTH: 20
<212> TYPE: DNA
<213> ORGANISM: Artificial Sequence
<220> FEATURE:
<223> OTHER INFORMATION: A forward PCR primer for HPV30 gene.

<400> SEQUENCE: 9
actaaggtgc ggttgtgtcc                                              20

<210> SEQ ID NO 10
<211> LENGTH: 20
<212> TYPE: DNA
<213> ORGANISM: Artificial Sequence
<220> FEATURE:
<223> OTHER INFORMATION: A reverse PCR primer for HPV30 gene.

<400> SEQUENCE: 10
ataaggcgag gcgtcttacg                                              20

<210> SEQ ID NO 11
<211> LENGTH: 22
<212> TYPE: DNA
<213> ORGANISM: Artificial Sequence
<220> FEATURE:
<223> OTHER INFORMATION: A forward PCR primer for HPV31 gene.

<400> SEQUENCE: 11
gggcgtctgc aactactact tc                                           22

<210> SEQ ID NO 12
<211> LENGTH: 20
<212> TYPE: DNA
<213> ORGANISM: Artificial Sequence
<220> FEATURE:
<223> OTHER INFORMATION: A reverse PCR primer for HPV31 gene.

<400> SEQUENCE: 12
acacttgtgg cgttgtaggg                                              20

<210> SEQ ID NO 13
<211> LENGTH: 20
<212> TYPE: DNA
<213> ORGANISM: Artificial Sequence
<220> FEATURE:
<223> OTHER INFORMATION: A forward PCR primer for HPV33 gene.

<400> SEQUENCE: 13
gtattggcac aggctctggt                                              20
```

<210> SEQ ID NO 14
<211> LENGTH: 18
<212> TYPE: DNA
<213> ORGANISM: Artificial Sequence
<220> FEATURE:
<223> OTHER INFORMATION: A reverse PCR primer for HPV33 gene.

<400> SEQUENCE: 14
aatgggcgtg cttgatgt                                          18

<210> SEQ ID NO 15
<211> LENGTH: 20
<212> TYPE: DNA
<213> ORGANISM: Artificial Sequence
<220> FEATURE:
<223> OTHER INFORMATION: A forward PCR primer for HPV34 gene.

<400> SEQUENCE: 15
caagctgagc aagcctggta                                        20

<210> SEQ ID NO 16
<211> LENGTH: 20
<212> TYPE: DNA
<213> ORGANISM: Artificial Sequence
<220> FEATURE:
<223> OTHER INFORMATION: A reverse PCR primer for HPV34 gene.

<400> SEQUENCE: 16
taggcgtctg gaacagttgg                                        20

<210> SEQ ID NO 17
<211> LENGTH: 20
<212> TYPE: DNA
<213> ORGANISM: Artificial Sequence
<220> FEATURE:
<223> OTHER INFORMATION: A forward PCR primer for HPV35 gene.

<400> SEQUENCE: 17
ccacttagca gcgtgagctt                                        20

<210> SEQ ID NO 18
<211> LENGTH: 20
<212> TYPE: DNA
<213> ORGANISM: Artificial Sequence
<220> FEATURE:
<223> OTHER INFORMATION: A reverse PCR primer for HPV35 gene.

<400> SEQUENCE: 18
gtctcgcgtt ggagtctcat                                        20

<210> SEQ ID NO 19
<211> LENGTH: 20
<212> TYPE: DNA
<213> ORGANISM: Artificial Sequence
<220> FEATURE:
<223> OTHER INFORMATION: A forward PCR primer for HPV39 gene.

<400> SEQUENCE: 19
tagttcacgc tgagccctct                                        20

<210> SEQ ID NO 20
<211> LENGTH: 20
<212> TYPE: DNA
<213> ORGANISM: Artificial Sequence
<220> FEATURE:
<223> OTHER INFORMATION: A reverse PCR primer for HPV39 gene.

```
<400> SEQUENCE: 20
aggtggaggc aaatacacca                                               20

<210> SEQ ID NO 21
<211> LENGTH: 19
<212> TYPE: DNA
<213> ORGANISM: Artificial Sequence
<220> FEATURE:
<223> OTHER INFORMATION: A forward PCR primer for HPV40 gene.

<400> SEQUENCE: 21
tgcagtttga gcagccatc                                                19

<210> SEQ ID NO 22
<211> LENGTH: 20
<212> TYPE: DNA
<213> ORGANISM: Artificial Sequence
<220> FEATURE:
<223> OTHER INFORMATION: A reverse PCR primer for HPV40 gene.

<400> SEQUENCE: 22
ccgtggcaag aggtatggat                                               20

<210> SEQ ID NO 23
<211> LENGTH: 20
<212> TYPE: DNA
<213> ORGANISM: Artificial Sequence
<220> FEATURE:
<223> OTHER INFORMATION: A forward PCR primer for HPV42 gene.

<400> SEQUENCE: 23
ccccgtttgt ccactacatc                                               20

<210> SEQ ID NO 24
<211> LENGTH: 20
<212> TYPE: DNA
<213> ORGANISM: Artificial Sequence
<220> FEATURE:
<223> OTHER INFORMATION: A reverse PCR primer for HPV42 gene.

<400> SEQUENCE: 24
gcgcctacgc caaaaataac                                               20

<210> SEQ ID NO 25
<211> LENGTH: 20
<212> TYPE: DNA
<213> ORGANISM: Artificial Sequence
<220> FEATURE:
<223> OTHER INFORMATION: A forward PCR primer for HPV45 gene.

<400> SEQUENCE: 25
taagccccat tgctgctaca                                               20

<210> SEQ ID NO 26
<211> LENGTH: 21
<212> TYPE: DNA
<213> ORGANISM: Artificial Sequence
<220> FEATURE:
<223> OTHER INFORMATION: A reverse PCR primer for HPV45 gene.

<400> SEQUENCE: 26
cagcagtaga aggcatggtc a                                             21

<210> SEQ ID NO 27
<211> LENGTH: 20
<212> TYPE: DNA
```

<213> ORGANISM: Artificial Sequence
<220> FEATURE:
<223> OTHER INFORMATION: A forward PCR primer for HPV51 gene.

<400> SEQUENCE: 27
gccatagtca ggcaaacgag                                             20

<210> SEQ ID NO 28
<211> LENGTH: 20
<212> TYPE: DNA
<213> ORGANISM: Artificial Sequence
<220> FEATURE:
<223> OTHER INFORMATION: A reverse PCR primer for HPV51 gene.

<400> SEQUENCE: 28
ctgctaccat tggggaaacg                                             20

<210> SEQ ID NO 29
<211> LENGTH: 20
<212> TYPE: DNA
<213> ORGANISM: Artificial Sequence
<220> FEATURE:
<223> OTHER INFORMATION: A forward PCR primer for HPV52 gene.

<400> SEQUENCE: 29
atagcactgc gacggacctt                                             20

<210> SEQ ID NO 30
<211> LENGTH: 21
<212> TYPE: DNA
<213> ORGANISM: Artificial Sequence
<220> FEATURE:
<223> OTHER INFORMATION: A reverse PCR primer for HPV52 gene.

<400> SEQUENCE: 30
ccgctgtctt ctacgtgaca t                                           21

<210> SEQ ID NO 31
<211> LENGTH: 20
<212> TYPE: DNA
<213> ORGANISM: Artificial Sequence
<220> FEATURE:
<223> OTHER INFORMATION: A forward PCR primer for HPV53 gene.

<400> SEQUENCE: 31
tacggttttg cagcaacagg                                             20

<210> SEQ ID NO 32
<211> LENGTH: 20
<212> TYPE: DNA
<213> ORGANISM: Artificial Sequence
<220> FEATURE:
<223> OTHER INFORMATION: A reverse PCR primer for HPV53 gene.

<400> SEQUENCE: 32
gcagctccag caatggttta                                             20

<210> SEQ ID NO 33
<211> LENGTH: 20
<212> TYPE: DNA
<213> ORGANISM: Artificial Sequence
<220> FEATURE:
<223> OTHER INFORMATION: A forward PCR primer for HPV54 gene.

<400> SEQUENCE: 33
accagccaat actgctgcta                                             20

```
<210> SEQ ID NO 34
<211> LENGTH: 20
<212> TYPE: DNA
<213> ORGANISM: Artificial Sequence
<220> FEATURE:
<223> OTHER INFORMATION: A reverse PCR primer for HPV54 gene.

<400> SEQUENCE: 34
agcaggttac acaggcatc                                                20

<210> SEQ ID NO 35
<211> LENGTH: 19
<212> TYPE: DNA
<213> ORGANISM: Artificial Sequence
<220> FEATURE:
<223> OTHER INFORMATION: A forward PCR primer for HPV56 gene.

<400> SEQUENCE: 35
ccgggaagga gtaaaacgg                                                19

<210> SEQ ID NO 36
<211> LENGTH: 20
<212> TYPE: DNA
<213> ORGANISM: Artificial Sequence
<220> FEATURE:
<223> OTHER INFORMATION: A reverse PCR primer for HPV56 gene.

<400> SEQUENCE: 36
cctgcaattg ttgtgttggc                                               20

<210> SEQ ID NO 37
<211> LENGTH: 20
<212> TYPE: DNA
<213> ORGANISM: Artificial Sequence
<220> FEATURE:
<223> OTHER INFORMATION: A forward PCR primer for HPV58 gene.

<400> SEQUENCE: 37
cattggtaca gggtcgggta                                               20

<210> SEQ ID NO 38
<211> LENGTH: 19
<212> TYPE: DNA
<213> ORGANISM: Artificial Sequence
<220> FEATURE:
<223> OTHER INFORMATION: A reverse PCR primer for HPV58 gene.

<400> SEQUENCE: 38
atccaaaggc cccacagta                                                19

<210> SEQ ID NO 39
<211> LENGTH: 20
<212> TYPE: DNA
<213> ORGANISM: Artificial Sequence
<220> FEATURE:
<223> OTHER INFORMATION: A forward PCR primer for HPV59 gene.

<400> SEQUENCE: 39
gttttgcaaa ggggaactgc                                               20

<210> SEQ ID NO 40
<211> LENGTH: 20
<212> TYPE: DNA
<213> ORGANISM: Artificial Sequence
<220> FEATURE:
<223> OTHER INFORMATION: A reverse PCR primer for HPV59 gene.
```

-continued

<400> SEQUENCE: 40
cgcttgtcgt tgctgtctta                                               20

<210> SEQ ID NO 41
<211> LENGTH: 22
<212> TYPE: DNA
<213> ORGANISM: Artificial Sequence
<220> FEATURE:
<223> OTHER INFORMATION: A forward PCR primer for HPV61 gene.

<400> SEQUENCE: 41
ccgtcctcgt ccctagtat aa                                             22

<210> SEQ ID NO 42
<211> LENGTH: 21
<212> TYPE: DNA
<213> ORGANISM: Artificial Sequence
<220> FEATURE:
<223> OTHER INFORMATION: A reverse PCR primer for HPV61 gene.

<400> SEQUENCE: 42
gatgtcacag gcgtatcaag c                                             21

<210> SEQ ID NO 43
<211> LENGTH: 22
<212> TYPE: DNA
<213> ORGANISM: Artificial Sequence
<220> FEATURE:
<223> OTHER INFORMATION: A forward PCR primer for HPV66 gene.

<400> SEQUENCE: 43
ataggctgga tgacactgag gt                                            22

<210> SEQ ID NO 44
<211> LENGTH: 22
<212> TYPE: DNA
<213> ORGANISM: Artificial Sequence
<220> FEATURE:
<223> OTHER INFORMATION: A reverse PCR primer for HPV66 gene.

<400> SEQUENCE: 44
caccatgtca ccgtcctcta tc                                            22

<210> SEQ ID NO 45
<211> LENGTH: 22
<212> TYPE: DNA
<213> ORGANISM: Artificial Sequence
<220> FEATURE:
<223> OTHER INFORMATION: A forward PCR primer for HPV68 gene.

<400> SEQUENCE: 45
tgctacattt acctcccgtt cc                                            22

<210> SEQ ID NO 46
<211> LENGTH: 19
<212> TYPE: DNA
<213> ORGANISM: Artificial Sequence
<220> FEATURE:
<223> OTHER INFORMATION: A reverse PCR primer for HPV68 gene.

<400> SEQUENCE: 46
aatgccagtg cgtgttacg                                                19

<210> SEQ ID NO 47
<211> LENGTH: 20
<212> TYPE: DNA

```
<213> ORGANISM: Artificial Sequence
<220> FEATURE:
<223> OTHER INFORMATION: A forward PCR primer for G3PDH gene.

<400> SEQUENCE: 47
cagcctcaag atcatcagca                                              20

<210> SEQ ID NO 48
<211> LENGTH: 20
<212> TYPE: DNA
<213> ORGANISM: Artificial Sequence
<220> FEATURE:
<223> OTHER INFORMATION: A reverse PCR primer for G3PDH gene.

<400> SEQUENCE: 48
aaaggtggag gagtgggtgt                                              20

<210> SEQ ID NO 49
<211> LENGTH: 70
<212> TYPE: DNA
<213> ORGANISM: Artificial Sequence
<220> FEATURE:
<223> OTHER INFORMATION: A probe for detection of HPV6 gene.

<400> SEQUENCE: 49
caccctgtga ctcagtggct gttgcacgcg ttttggtttg cacgcgcctt acacacataa   60
gtaatataca                                                         70

<210> SEQ ID NO 50
<211> LENGTH: 70
<212> TYPE: DNA
<213> ORGANISM: Artificial Sequence
<220> FEATURE:
<223> OTHER INFORMATION: A probe for detection of HPV11 gene.

<400> SEQUENCE: 50
gccctgccaa gtatcttgcc aacaacacac ctggccaggg cgcggtattg catgactaat   60
gtacaataaa                                                         70

<210> SEQ ID NO 51
<211> LENGTH: 70
<212> TYPE: DNA
<213> ORGANISM: Artificial Sequence
<220> FEATURE:
<223> OTHER INFORMATION: A probe for detection of HPV16 gene.

<400> SEQUENCE: 51
cgtttcctgc ttgccatgcg tgccaaatcc ctgttttcct gacctgcact gcttgccaac   60
cattccattg                                                         70

<210> SEQ ID NO 52
<211> LENGTH: 70
<212> TYPE: DNA
<213> ORGANISM: Artificial Sequence
<220> FEATURE:
<223> OTHER INFORMATION: A probe for detection of HPV18 gene.

<400> SEQUENCE: 52
attgcgtcgc aagcccacca taggccctcg caaacgttct gctccatctg ccactacgtc   60
ttctaaacct                                                         70

<210> SEQ ID NO 53
<211> LENGTH: 70
<212> TYPE: DNA
```

<213> ORGANISM: Artificial Sequence
<220> FEATURE:
<223> OTHER INFORMATION: A probe for detection of HPV30 gene.

<400> SEQUENCE: 53
ggcatttagg tagcaattta ggtggcgtcc ctatgtcctc cacccttttt ggttgttgca    60
caccactgtg                                                           70

<210> SEQ ID NO 54
<211> LENGTH: 70
<212> TYPE: DNA
<213> ORGANISM: Artificial Sequence
<220> FEATURE:
<223> OTHER INFORMATION: A probe for detection of HPV31 gene.

<400> SEQUENCE: 54
cacctgccac acataatgtt tccccttcta ctgctgtaca gtccacatct gctgtgtctg    60
cctatgtacc                                                           70

<210> SEQ ID NO 55
<211> LENGTH: 70
<212> TYPE: DNA
<213> ORGANISM: Artificial Sequence
<220> FEATURE:
<223> OTHER INFORMATION: A probe for detection of HPV33 gene.

<400> SEQUENCE: 55
acctattggt actgacccac ctacagctgc aatccccttg cagcctatac gtcctccggt    60
tactgtagac                                                           70

<210> SEQ ID NO 56
<211> LENGTH: 70
<212> TYPE: DNA
<213> ORGANISM: Artificial Sequence
<220> FEATURE:
<223> OTHER INFORMATION: A probe for detection of HPV34 gene.

<400> SEQUENCE: 56
gcagcagatg tcagtccaca gtgtgtctta ccattgagag cacacacgct gacctattag    60
tgttagaaga                                                           70

<210> SEQ ID NO 57
<211> LENGTH: 70
<212> TYPE: DNA
<213> ORGANISM: Artificial Sequence
<220> FEATURE:
<223> OTHER INFORMATION: A probe for detection of HPV35 gene.

<400> SEQUENCE: 57
caggtagagg ggcatgatac agttgaacaa tgtagtatgg gcagtgggga tagtataacc    60
tctagtagcg                                                           70

<210> SEQ ID NO 58
<211> LENGTH: 71
<212> TYPE: DNA
<213> ORGANISM: Artificial Sequence
<220> FEATURE:
<223> OTHER INFORMATION: A probe for detection of HPV39 gene.

<400> SEQUENCE: 58
gggattcggg cactacatat aacacaggct cactaccttc tgtggcttct tcagcatcta    60
ctaaatatgc c                                                         71

<210> SEQ ID NO 59
<211> LENGTH: 70
<212> TYPE: DNA
<213> ORGANISM: Artificial Sequence
<220> FEATURE:
<223> OTHER INFORMATION: A probe for detection of HPV40 gene.

<400> SEQUENCE: 59
cggcaccaca tacactggag acaccacata cactagagac accactggac actactgatg    60
ccctgtttga    70

<210> SEQ ID NO 60
<211> LENGTH: 70
<212> TYPE: DNA
<213> ORGANISM: Artificial Sequence
<220> FEATURE:
<223> OTHER INFORMATION: A probe for detection of HPV42 gene.

<400> SEQUENCE: 60
actgtgcatg tgggccctga tttatctgtt gtggaccacc catgggacag taccccaacg    60
tctgtaatgc    70

<210> SEQ ID NO 61
<211> LENGTH: 70
<212> TYPE: DNA
<213> ORGANISM: Artificial Sequence
<220> FEATURE:
<223> OTHER INFORMATION: A probe for detection of HPV45 gene.

<400> SEQUENCE: 61
gtgctacaaa tgatagtgac ctgtttgatg tatatgcaga cttcccacct cctgcgtcca    60
ctacacctag    70

<210> SEQ ID NO 62
<211> LENGTH: 70
<212> TYPE: DNA
<213> ORGANISM: Artificial Sequence
<220> FEATURE:
<223> OTHER INFORMATION: A probe for detection of HPV51 gene.

<400> SEQUENCE: 62
gatgggcaac atggcggttc acagaacagt gtgtgtagta gcggggggg cagtgttatg    60 gatgtggaaa    70

<210> SEQ ID NO 63
<211> LENGTH: 70
<212> TYPE: DNA
<213> ORGANISM: Artificial Sequence
<220> FEATURE:
<223> OTHER INFORMATION: A probe for detection of HPV52 gene.

<400> SEQUENCE: 63
caagcagtcc ggaaagtgct gggcaagatg gtgtagaaaa acatggtagt ccgcgtgcaa    60
aacacatttg    70

<210> SEQ ID NO 64
<211> LENGTH: 69
<212> TYPE: DNA
<213> ORGANISM: Artificial Sequence
<220> FEATURE:
<223> OTHER INFORMATION: A probe for detection of HPV53 gene.

<400> SEQUENCE: 64

```
cacccaggac atccatggat cgtcagttat ttgaaaatac agaagagcga ccacgtacat    60
tgcaccagc                                                           69

<210> SEQ ID NO 65
<211> LENGTH: 70
<212> TYPE: DNA
<213> ORGANISM: Artificial Sequence
<220> FEATURE:
<223> OTHER INFORMATION: A probe for detection of HPV54 gene.

<400> SEQUENCE: 65
gtgtatatag tgaggtatgt atggtgagta tggtagtgag tgcatgcagg cctgcagtga    60
ctgaggtgag                                                          70

<210> SEQ ID NO 66
<211> LENGTH: 70
<212> TYPE: DNA
<213> ORGANISM: Artificial Sequence
<220> FEATURE:
<223> OTHER INFORMATION: A probe for detection of HPV56 gene.

<400> SEQUENCE: 66
gaggtacagg gacgtgggtg cgggaataca caaaatggag gctcacaaaa cagtacctat    60
agtaacaata                                                          70

<210> SEQ ID NO 67
<211> LENGTH: 70
<212> TYPE: DNA
<213> ORGANISM: Artificial Sequence
<220> FEATURE:
<223> OTHER INFORMATION: A probe for detection of HPV58 gene.

<400> SEQUENCE: 67
atatgtgccc cttggtagta ccccaccgtc tgaggctata cctttacagc ccatacgtcc    60
cccagttacc                                                          70

<210> SEQ ID NO 68
<211> LENGTH: 71
<212> TYPE: DNA
<213> ORGANISM: Artificial Sequence
<220> FEATURE:
<223> OTHER INFORMATION: A probe for detection of HPV59 gene.

<400> SEQUENCE: 68
gaggctgaaa ccaagacacc gttacatgag ctgctgatac gctgttatag atgcctaaaa    60
cctctatgtc c                                                        71

<210> SEQ ID NO 69
<211> LENGTH: 70
<212> TYPE: DNA
<213> ORGANISM: Artificial Sequence
<220> FEATURE:
<223> OTHER INFORMATION: A probe for detection of HPV61 gene.

<400> SEQUENCE: 69
tatgctgacc ctgaggtgtt ggatcttcct gcacaacata cacaacccac acttacagta    60 cagggcccctt                                                         70

<210> SEQ ID NO 70
<211> LENGTH: 70
<212> TYPE: DNA
<213> ORGANISM: Artificial Sequence
<220> FEATURE:
```

-continued

```
<223> OTHER INFORMATION: A probe for detection of HPV66 gene.

<400> SEQUENCE: 70
gcaccagcat taggggaaca ttggactaag ggcgcggtgt gtaagtctac accaggtaat    60
acagggatt                                                           70

<210> SEQ ID NO 71
<211> LENGTH: 70
<212> TYPE: DNA
<213> ORGANISM: Artificial Sequence
<220> FEATURE:
<223> OTHER INFORMATION: A probe for detection of HPV68 gene.

<400> SEQUENCE: 71
tgttgtgtta ccagcaacgt ctccacagtt gcctttaaca ccctctacac caattgatac    60
aacctatgcc                                                          70

<210> SEQ ID NO 72
<211> LENGTH: 70
<212> TYPE: DNA
<213> ORGANISM: Artificial Sequence
<220> FEATURE:
<223> OTHER INFORMATION: A probe for detection of G3PDH gene.

<400> SEQUENCE: 72
aaacctgcca aatatgatga catcaagaag gtggtgaagc aggcgtcgga gggcccctc     60 aagggcatcc                                                          70
```